United States Patent [19]

Livingston et al.

[11] Patent Number: 4,921,638
[45] Date of Patent: May 1, 1990

[54] 17β-CYANO-9α,17α-DIHYDROXYANDROST-4-EN-3-ONE

[75] Inventors: Douglas A. Livingston, Oshteme Township, Kalamazoo County; Bruce A. Pearlman, Kalamazoo, both of Mich.; Scott Denmark, Urbana, Ill.; Joel E. Huber, Boston, Mass.

[73] Assignee: The Upjohn Company, Kalamazoo, Mich.

[21] Appl. No.: 252,639

[22] Filed: Oct. 3, 1988

Related U.S. Application Data

[63] Continuation-in-part of PCT US87/02818, filed Nov. 2, 1987, which is a continuation-in-part of Ser. No. 20,457, Mar. 2, 1987, abandoned, which is a continuation-in-part of Ser. No. 927,633, Nov. 5, 1986, abandoned.

[51] Int. Cl.$^5$ ............................................... C07J 1/00
[52] U.S. Cl. ................................. 552/610; 552/526; 552/505; 552/598; 552/596; 552/595; 552/607; 552/581; 552/529; 552/597; 552/580; 552/608; 540/4; 540/94
[58] Field of Search ................................. 260/397.4

[56] References Cited

U.S. PATENT DOCUMENTS 3,496,169  2/1970  Nagata et al. ............... 260/239.55
4,548,748  10/1985  Van Rheenen ............... 260/239.55

FOREIGN PATENT DOCUMENTS 263569  9/1987  European Pat. Off. .

OTHER PUBLICATIONS

J. Am. Chem. Soc., 75, 650 (1953).
Steroids, 28, 89 (1976).
Helv. Chim. Acta, 33, 1093 (1950).
Helv. Chim. Acta, 29, 1580 (1946).
Helv. Chim. Acta, 21, 1317 (1938).

Primary Examiner—Joseph A. Lipovsky
Attorney, Agent, or Firm—Bruce Stein

[57] ABSTRACT

The invention is the compound 17β-cyano-9α, 17α-dihydroxyandrost-4-en-3-one (I) which is particularly useful as an intermediate in the production of the 17α-halo silyl ethers (II).

1 Claim, No Drawings

17β-CYANO-9α,17α-DIHYDROXYANDROST-4-EN-3-ONE

CROSS-REFERENCE TO RELATED APPLICATIONS

The present patent application is a continuation-in-part of copending PCT application 87/02818 filed November 2, 1987, which was a continuation-in-part patent application of copending U.S. patent application Ser. No. 020,457 filed March 2, 1987, now abandoned, which was a continuation-in-part patent application of copending U.S. Ser. No. 927,633 filed November 5, 1986, now abandoned.

BACKGROUND OF THE INVENTION

1. Field of the Invention

The invention includes a 9α-hydroxy steroidal 17-cyanohydrin useful as an intermediate in the synthesis of the novel 17β-cyano-17α-halo silyl ether intermediates.

The invention includes 17α-halo silyl ether steroidal 17β-cyanohydrins useful as intermediates in the production of progesterones, 17-hydroxyprogesterones and corticoid pharmaceuticals as well as processes to produce and use the intermediates.

2. Description of the Related Art

Steroidal 17-cyanohydrins are known. See for example, U.S. Pat. Nos. 3,496,169 and 4,548,748; J. Am. Chem. Soc., 75, 650 (1953), Steroids 28, 89 (1976); Helv. Chim. Acta 33, 1093 (1950); Helv. Chim Acta 29, 1580 (1946), Helv. Chim. Acta 21, 1317 (1938) and East German Patent No. 147,669.

European Patent publication 263,569 (WO88/02753) discloses (Example 9) 17β-cyano-9α,17α-dihydroxyandrost-4-en-3-one.

SUMMARY OF THE INVENTION

Disclosed is 17β-cyano-9α,17α-dihydroxyandrost-4-en-3-one.

DETAILED DESCRIPTION OF THE INVENTION

17β-Cyano-9α,17α-dihydroxyandrost-4-en-3-one (I) is prepared from the corresponding 17-keto steroid, 9α-hydroxyandrost-4-ene-3,17-dione (O) by the procedure of EXAMPLES 85 and 87; the preferred procedure is that of EXAMPLE 87. 17β-Cyano-9α,17α-dihydroxyandrost-4-en-3-one (I) is dehydrated to 17β-cyano-17α-hydroxyandrosta-4,9(11)-dien-3-one (I), a known compound (U.S. Pat. No. 4,548,748, EXAMPLE 2), which is useful as an intermediate in the production of the 17α-halo silyl ether intermediates (II) of the present invention, see EXAMPLES 86 and 88; the preferred procedure is that of EXAMPLE 88.

The α-halo silyl ether (II) is prepared from the corresponding 17-cyano-17-hydroxy steroid (I) by reacting it with the appropriate α-halo silyl ether adduct (IV). It is preferred that the α-halo silyl ether (II) be the α-halo silyl ether (IIA). The 17-cyano-17-hydroxy steroids (I) are known to those skilled in the art or can be readily prepared from known 17-keto androstanes (O) by methods known to those skilled in the art, see for example U.S. Pat. No. 4,500,461, for β-cyanohydrins, and Tetrahedron Letters 24, 4559 (1983) for α-cyanohydrins. With the 17-cyano-17-hydroxy steroids (I) and the α-sustituted silyl ethers (II), the cyano group at C$_{17}$ can be in either the α- or β-configuration; it is preferred that the cyano group at C$_{17}$ be in the β-configuration giving 17β-cyano-17α-hydroxy steroids (I) and 17β-cyano-17α-silyl ethers (II). Therefore, when the term "17-cyano-17-hydroxy" is used in the present patent application it means and includes both C$_{17}$ epimers, except when referring to particular steroidal compounds. The 17α-cyano-17β-hydroxy steroids (I) and the 17β-cyano-17α-hydroxy steroids (I) are both operable in all aspects of the present invention, and can be prepared by methods known to those skilled in the art. For example, PREPARATIONS 7 and 9 are applications of the method described in Tetrahedron Letters 24, 4559 (1983).

The 17-cyano-17-hydroxy steroid (I) is first slurried with a dry organic solvent. Suitable organic solvents include methylene chloride, THF, toluene, dichloroethane, DMF, dimethoxyethane, acetonitrile and mixtures thereof. It is preferred that the organic solvent be methylene chloride or DMF. The reaction mixture is then preferably cooled to about −10° to 0°. The 17-cyano-17-hydroxy steroid (I) is then contacted with the α-halo silyl ether adduct (IV). The α-halo silyl ether adducts (IV) are either known to those skilled in the art or can be readily prepared from known compounds by means known those skilled in the art. The α-halo silyl halides (IV), for example, can be easily prepared by halogenation of the corresponding alkyl silyl halides. Thus, chloromethyldimethylchlorosilane (IV) is prepared by chlorination of trimethylchlorosilane. Likewise dichloromethyldimethylchlorosilane is prepared by dichlorination of trimethylchlorosilane and chloromethyltrichlorosilane by chlorination of methyltrichlorosilane, etc. See Tetrahedron 26, 279 (1970) and J. Am. Chem. Soc., 73, 824 (1951). It is preferred that the contacting be in the presence of an acid scavenger selected from the group consisting of alkyl lithium, calcium and sodium hydride, mesityl lithium, tert-butyllithium, sec-butyllithium, n-butyllithium, lithium t-butoxide, potassium t-butoxide, sodium tertiary amylate, disodiocyanamide, dilithio N,N'-diphenylhydrazine, and metal-N(X$_7$) (X$_8$) where metal is lithium, sodium, potassium or magnesium, X$_7$ is C$_1$–C$_7$ alkyl, trimethylsilyl and cyclohexyl, X$_8$ is X$_7$ and 1-(1-phenylpentyl), and the metal salts of piperidine, 2,2,6,6-tetramethylpiperidine, 2,6-di-t-butylpiperidine, 2,6-dimethylpiperidine, ethylenediamine, trimethylethylenediamine, morpholine, imidazole, 2-aminopyridine and amines. Acid scavengers are compounds which scavenge or trap free protons in solution and thereby prevent undesirable side reactions. Amine acid scavengers are of the formula NX$_{12}$X$_{13}$X$_{14}$ where X$_{12}$, X$_{13}$ and X$_{14}$ the same or different and are -H, -φ, -CH$_2$-φ, -CH$_2$CH$_2$-φ, methylphenyl, C$_1$–C$_9$ alkyl optionally substituted with 1 or more oxygen or nitrogen atoms, the alkyl groups can be cyclized with the attached nitrogen atom and 1 or more oxygen or nitrogen atoms to form 1 through 3 rings selected from the group consisting of pyridine optionally substituted with 1 through 3 C$_1$–C$_4$ alkyl, pollyallylamine, polyethylenimine, benzylated polyethylenimine, polyvinylpyridine, biazabicyclo[2.2.2]octane, imidazole, N-methylmorpholine, N-methylpiperidine, N-methylimidazole, 2-methylimidazole, 1,8-diazabicyclo[5.4.0]undec-7-ene and 1,5-diazabicyclo[4.3.0]non-5-ene with the proviso that not more than 2 of X$_{12}$, X$_{13}$ and X$_{14}$ can be -H. Preferred acid scavengers include triethylamine, tributylamine, diisopropylethylamine, trimethylamine, pyridine, imidazole, N-methylmorpholine, N-methylpiperidine, N-methylimidazole, 2-methylimidazole, most preferred are TEA and imidazole. The acid scavenger should be added in an amount from about 1 to about 5 equivalents; preferably about 1.3 equivalents if TEA is used. It is preferred that the contacting take place in the presence of a silylation catalyst. Suitable silylation catalyst include pyridine substituted in the 4- position with $-NX_{16}X_{17}$ where $X_{16}$ and $X_{17}$ are the same or different and are $C_1$–$C_5$ alkyl and where the alkyl groups can optionally be taken together with the attached nitrogen atom and 1 or more nitrogen or oxygen atoms to form a heterocyclic ring, pyridine-N-oxide, benzimidazole, substituted imidazoles where the substituent is $C_1$–$C_5$ alkyl or -$\phi$, preferred is 4-dimethylaminopyridine or imidazole. The silylation catalyst should be added in an amount of about 0.5 to 10 mole %; preferably about 2 mole %. With regard to the $\alpha$-halo silyl ether adduct (IV) at least 1 equivalent, preferably about 1.1 to about 1.5 equivalents, more preferably about 1.2 equivalents should be used. The reaction is monitored by TLC, HPLC, etc and is usually complete within 2 hr (if a catalyst is used) depending on the temperature. For example, with chloromethyldimethylchlorosilane (IV) using TEA as the acid scavenger and 4-dimethylaminopyridine as the silylation catalyst the reaction is complete in less than 1 hr at $-5°$. The reaction can be quenched by adding the reaction mixture to a quenching agent which permits easy isolation of the $\alpha$-halo silyl ether (II). In some cases one can simply filter off the acid scavenger-acid complex. One can often carry on the reaction of the $\alpha$-halo silyl ether (II) directly without its isolation, in this case quenching of the reaction mixture is not necessary, see EXAMPLE 74. Examples of quenching agents include, for example, phosphate buffer, ammonium chloride buffer and dilute acetic acid. The pH of the quench mixture is controlled to avoid hydrolyzing acid or base sensitive functions or the silyl ether itself. Generally, phosphate buffer (pH 4.5) is preferred, a potassium or sodium dihydrogen phosphate solution. The $\alpha$-halo silyl ether (II) is obtained by extraction in the usual manner.

In situtations where either or both of $X_1$ and $X_2$ is an ether, $-O-X_{1-1}$ and $-OX_{2-1}$ respectively, or -F, the starting $\alpha$-halo silyl ether adduct (IV) preferably has $X_1$ and/or $X_2$ as -Cl or -Br which can be selectively replaced to give the desired product; see EXAMPLES 48–53. The $\alpha$-halo silyl ether adduct (IV) is reacted first with a 17-cyano-17-hydroxy steroid (I), then with an alcohol. This is the preferred order of displacement, although any order will be operable and deemed equivalent. For $X_1$ or $X_2$ to be -F, the $\alpha$-halo substituted adduct (IV) must be treated with a suitable fluoride source which includes potassium, sodium or tetrabutylammonium fluoride. Although these $\alpha$-halo silyl ethers (IV) are operable in all aspects of the present invention, they are particularly suited for the direct preparation of the corticoids (VII) using a Type A reducing agent followed by an oxidizing agent.

The $\alpha$-halo silyl ethers (II) are useful in the production of progesterones (V), hydroxyprogesterones (VI), corticoids (VII) and 21-halo corticoids (III) which are intermediates in the production of corticoids (VII) as is explained below. Each of the $\alpha$-halo silyl ethers (II) disclosed here can be transformed to the corresponding progesterone (V), hydroxyprogesterone (VI), corticoid (VII) and 21-halo corticoid (III) as disclosed and exemplified below.

It is preferred that the $\alpha$-halo silyl ether (II) be the $\alpha$-halo silyl ether (IIA). It is preferred that the cyano group at $C_{17}$ be in the $\beta$-configuration. It is preferred that the $\alpha$-halo silyl ether (II) be a $\Delta^4$-3-keto steroid or a $\Delta^{1,4}$-3-keto steroid or protected forms (A-VI, A-VIII and A-IX) thereof. It is preferred that the C-ring contain (1) $\Delta^{9(11)}$ functionality, (2) have $\alpha$-$R_9$ be -H or -F when $R_{11}$ is $=O$ or $\alpha$-$R_{11-5}$:$\beta$-$R_{11-6}$, where one of $R_{11-5}$ and $R_{11-6}$ is -H, and the other of $R_{11-5}$ and $R_{11-6}$ is -H or -OH, and (3) $\alpha$-$R_9$ is -H, -F, -Cl or -Br when $R_{11}$ is $\alpha$-$R_{11-5}$:$\beta$-$R_{11-6}$, where one of $R_{11-5}$ and $R_{11-6}$ is -H, and the other of $R_{11-5}$ and $R_{11-6}$ is -H, -OH, $-SiX_{26}X_{27}X_{28}$ or $-Si(X_1)(X_2)-C(X_3)(X_4)(X_5)$. It is preferred that one of $R_{16-1}$ and $R_{16-2}$ is -H and the other is -H or -CH$_3$. It is preferred that $X_1$ is -CH$_3$ or $-OX_{1-1}$ and $X_2$ is -CH$_3$ or $-OX_{2-1}$, $X_3$ is -H, -Cl, -Br and $X_5$ is -Cl or -Br. It is more preferred that $X_1$ and $X_2$ are -CH$_3$, $X_3$ is -H and $X_5$ is -Cl. Preferred $\alpha$-halo silyl ethers (II) the compounds of EXAMPLES 1–3, 7–13, 16, 19–21, 25, 28–39, 40A, 41–48, 54, 57–59, 67, 70–72 and 82. More preferred are the $\alpha$-halo silyl ethers (II) of EXAMPLES 1, 3, 7, 33, 36, 43 and 45.

The $\alpha$-halo silyl ethers (II) can be prepared from other $\alpha$-halo silyl ethers (II) by a displacement reaction using iodide, bromide or chloride. The halo group $\alpha$- to silicon ($X_3$ or $X_5$) is easy to exchange for a different halide by a displacement reaction. For example, with the $\alpha$-halo silyl ether (II) when $X_1$ and $X_2$ are -CH$_3$, $X_3$ and $X_4$ are -H and $X_5$ is -Br, it is possible to convert $X_5$ into -Cl or -I by contacting the $\alpha$-halo silyl ether (II) with chloride or iodide ion. This is the preferred method of preparing the $\alpha$-halo silyl ether (II) where $X_5$ is -I, see EXAMPLES 58 and 67. This also means it is important in the operation of this invention that the $\alpha$-halo silyl ether (II) not be allowed to contact undersired halide ions for longer than is necessary. For example, if in the execution of EXAMPLE 2, 13 or 57, the reaction mixture is left in contact longer than necessary to complete silylation, significant amounts of the chloromethyldimethyl silyl ether (II) will form, by exchange of the -Br with chloride ions in the reaction from the TEA hydrochloride formed.

The $\alpha$-halo silyl ether (II) is transformed to the 21-halo corticoid (III) by contacting the $\alpha$-halo silyl ether (II) with at least one equivalent of a non-nucleophilic base followed by contacting (quenching) with a protiodesilation reagent and a nitrogen to oxygen exchange reagent. A non-nucleophilic base, is a base which is sufficiently strong to deprotinate $X_4$. Examples of non-nucleophilic bases include mesityl lithium, tert-butyllithium, sec-butyllithium, n-butyllithium, lithium t-butoxide, potassium t-butoxide, sodium tertiary amylate, disodiocyanamide, dilithio N,N'-diphenylhydrazine, and metal-N($X_7$)($X_8$) where metal is lithium, sodium, potassium or magnesium, $X_7$ is $C_1$–$C_7$ alkyl, trimethylsilyl and cyclohexyl, $X_8$ is $X_7$ and 1-(1-phenylpentyl), and the metal salts of piperidine, 2,2,6,6-tetramethylpiperidine, 2,6-di-t-butylpiperidine, 2,6-dimethylpiperidine, ethylenediamine, trimethylethylenediamine, morpholine, imidazole and 2-aminopyridine. Preferred non-nucleophilic bases are mesityl lithium, tert-butyllithium, sec-butyllithium, n-butyllithium, disodiocyanamide, dilithio N,N'-diphenylhydrazine, and metal-N-($X_7$)($X_8$) where metal is lithium, sodium, potassium or magnesium, $X_7$ is $C_1$–$C_7$ alkyl, trimethylsilyl and cyclohexyl, $X_8$ is $X_7$ and 1-(1-phenylpentyl), and the metal salts of piperidine, 2,2,6,6-tetramethylpiperidine, 2,6-di-t-butylpiperidine, 2,6-dimethylpiperidine, ethylenediamine, trimethylethylenediamine, morpholine, imidazole and 2-aminopyridine, more preferred is LDA. When $X_3$ and $X_5$ are -Cl or -Br it is preferred the non-mucleophilic base is one where $X_7$ and $X_8$ are trimethylsilyl. About 1 to about 4 equivalents of the non-nucleophilic base are used. At least 1 equivalent is required, preferably about 1.5 equivalents (in the absence of reactive functional groups in the molecule) should be used. If the α-halo silyl ether (II) has a hydroxyl group at $R_{11}$ and/or an unprotected A-ring (3-ketone) an additional equivalent for each reactive functionality is necessary as is known to those skilled in the art. For example, with a 11β-hydroxy-$\Delta^4$-3-keto α-halo silyl ether (II) (EXAMPLE 26), at least 3 equivalents are needed, one for the 11β-hydroxyl functionality, one for the A-ring and one for the reaction. When the reaction is complete as monitored by TLC or HPLC it is quenched a protiodesilation reagent and a nitrogen to oxygen exchange reagent. A protiodesilylation reagent is selected from the group consisting of (1) water or an alcohol and an acid where the alcohol is of the formula $R_{50}$-OH where $R_{50}$ is selected from the group consisting of $C_1$-$C_7$ alkyl, -φ, -CH$_2$-φ, -CH$_2$CH$_2$-OCH$_3$,
HO-$R_{51}$-OH where $R_{51}$ is $C_2$-$C_7$ alkyl,
propylene glycol,
ethylene glycol,
glycerol; where the acid is selected from the group consisting of HF, HCl, HBr, HI, H$_3$PO$_4$, H$_2$SO$_4$, perchloric, fluoroboric, NaHSO$_4$, NaH$_2$PO$_4$, polymeric sulfonic acid cation exchange resins, HOOC-(CH$_2$)$_n$-COOH where n is 0 through 12, tartaric acid, citric acid, B($X_{19}$)$_3$, Al($X_{19}$)$_4$, Sn($X_{19}$)$_4$, Sn($X_{19}$)$_2$ and Ti($X_{19}$)$_4$ where $X_{19}$ is -F, -Cl, -Br and -I, $R_{52}$-COOH and $R_{52}$-SO$_3$-H where $R_{52}$ is -H, $C_1$-$C_{12}$ alkyl, -φ, methylphenyl, -CF$_3$, -CCl$_3$, hydrochloride and hydrobromide salts of amines of the formula N$X_{12}X_{13}X_{14}$ where $X_{12}$, $X_{13}$ and $X_{14}$ the same or different and are -H, -φ, -CH$_2$-φ, -CH$_2$CH$_2$-φ, methylphenyl, $C_1$-$C_9$ alkyl optionally substituted with 1 or more oxygen or nitrogen atoms, the alkyl groups can be cyclized with the attached nitrogen atom and 1 or more oxygen or nitrogen atoms to form 1 through 3 rings with the proviso that at least 1 of $X_{12}$, $X_{13}$ and $X_{14}$ is -H; or (2) a fluoride salt where the fluoride salt is selected from the group consisting of BF$_3$, CsF, KF, NaF, LiF, LiBF$_4$ and n-(butyl)$_4$NF. The nitrogen to oxygen exchange reagent is selected from the group consisting of (1) water and an acid as is defined above or (2) a ketone of the formula $R_{53}$-CO-$R_{54}$ where $R_{53}$ and $R_{54}$ are the same or different and are $C_1$-$C_7$ alkyl, the alkyl groups can be taken together with the attached carbonyl group to form a saturated ring of from 5 to 7 members, an aldehyde of the formula $R_{55}$-CHO where $R_{55}$ is $C_1$-$C_5$ alkyl or -φ, or pyruvic acid. The simplist, easiest, cheapest and the preferred procedure is to use just one reagent which falls into both catagories. It is preferred that that reagent is water and an acid. It is preferred to use at least one equivalent of water and almost any acid is operable. It is preferred that the acid be selected from the group consisting of HF, HCl, HBr, HI, H$_3$PO$_4$, H$_2$SO$_4$, perchloric, fluoroboric, formic, acetic, propionic and oxalic. It is more preferred that the acid be HF, HCl, HBr, H$_2$SO$_4$, methanesulfonic and acetic. When $X_5$ is -Br it is preferred that the acid be HBr. In the case of a 3-keto steroid it is preferred to conduct the first step using besides the additional non-nucleophilic base 0.5 to 1.0 equivalents of a compound selected from the group consisting of Cl-Si-(CH$_3$)$_3$, (F$_3$C-CO)$_2$-O-, $X_{20}$-Si-$X_9X_{10}X_{11}$ where $X_9$, $X_{10}$ and $X_{11}$ are $C_1$-$C_5$ alkyl, -φ, -Cl, -O$X_{15}$ where $X_{15}$ is $C_{1-5}$ alkyl or -φ and where $X_{20}$ is -Cl or -Br, ($X_{18}$-CO)$_2$-O- where $X_{18}$ is -φ or t-butyl, $X_{18}$-CO-Cl. Preferred is chlorotrimethylsilane. The chlorotrimethylsilane can be added at any time during the addition of the non-nucleophilic base, but preferreably before the non-nucleophilic base is added. The non-nucleophilic base can be added to the α-halo silyl ether (II), or the α-halo silyl ether (II) can be added to the non-nucleophilic base. It is preferred to conduct the second step in the presence of an alcohol. The alcohol is not necessary but often increases the rate of hydrolysis. Examples of alcohols include $R_{50}$-OH where $R_{50}$ is selected from the group consisting of $C_1$-$C_7$ alkyl,-φ, -CH$_2$-φ, -CH$_2$CH$_2$-OCH$_3$, HO-$R_{51}$-OH where $R_{51}$ is $C_2$-$C_7$ alkyl, propylene glycol, ethylene glycol and glycerol. It is preferred that the alcohol be ethylene glycol, methanol or isopropanol. When the α-halo silyl ether (II) has a $\Delta^{1,4}$-3-keto A-ring, it is preferred that reaction sequence be as follows (1) contacting the α-halo silyl ether (II) with at least 1 equivalent of LiHMDS, (2) contacting the reaction mixture with at least 2 equivalents of a non-nucleophilic base and (3) contacting the reaction mixture of step (2) with at least one equivalent of water and an acid. It is more preferred that the reaction sequence be as follows (1) contacting the α-halo silyl ether (II) with at least 1 equivalent of LiHMDS, (2) trapping the C$_3$-enolate as an ether, (3) contacting the reaction mixture with at least 2 equivalents of a non-nucleophilic base and (4) contacting the reaction mixture of step (3) with at least 1 equivalent of water and an acid. The contacting of the first step should be performed at <80°, preferably from about 25° to about −80°. When the base is LDA the contacting should genrraly be at <−15° dependint on the α-halo silyl ether (II). Suitable solvents for the reaction include THF, dimethoxyethane, toluene, methyl t-butyl ether, cyclohexane and mixtures thereof. The solvent is preferably THF but in the situation where the LDA is in hexane, the preferred solvent is a THF/hexane mixture. Preferred 21-halo corticoids (III) are the compounds of EXAMPLES 5, 6, 17, 22, 26, 40B, 55, 60, 63, 75-77, 79, 80 and 83. More preferred are the 21-halo corticoids (III) of EXAMPLES 5, 17, 22, 75-77 and 83.

The 21-halo corticoids (III) are well known to those skilled in the art and are readily transformed to pharmaceutically useful corticoids by methods known to those skilled in the art and are themselves pharmaceutically useful see U.S. Pat. No. 4,619,921. For example, 21-chloro-17α-hydroxypregna-4,9(11)-diene-3,20-dione is known, see U.S. Pat. No. 4,357,279 (Example 5) and U.S. Pat. No. 4,342,702 (Example 5). 21-Bromo-17α-hydroxypregna-4,9(11)-diene-3,20-dione is known, see U.S. Pat. No. 4,041,055 (Example 59). Thus displacement with acylate gives 21-acyl corticoids, for exemple displacement with acetate gives 21-acetyl-17α-hydroxypregna-4,9(11)-diene-3,20-dione, useful in the preparation of hydrocortisone 21-acetate. Reduction of the 21-substituent with, for example, zinc and acetic acid gives 17-hydroxyprogesterones. When $R_{61}$ is -CH$_3$ the 17-hydroxyprogesterone is useful in the preparation of medroxyprogesterone acetate.

The α-halo silyl ether (II) can also be transformed to the corresponding 17-hydroxyprogesterone (VI) by contacting it with (1) an effective amount of a Type A reducing agent, (2) contacting the mixture of step (1) with a protiodesilation reagent and a nitrogen to oxygen exchange reagent. It is more preferred that the reaction sequence be contacting the α-halo silyl ether (II) with (1) two or more equivalents of a Type A reducing agent, (2) contacting the mixture of step (1) with an aprotic quenching agent and (3) contacting with a protiodesilation reagent and a nitrogen to oxygen exchange reagent. A type A reducing agent is a reagent which when reacted with an α-halo silyl ether (II) in an effective amount followed by reaction with an aprotic quenching agent, and a protiodesilation reagent and a nitrogen to oxygen exchange reagent produces a 17-hydroxyprogesterone (VI). Examples of Type A reducing agents include lithium and sodium complex with the following: anthracene, naphthacene, benzanthracene, 20-methylcholanthrene, nitrobenzene, metadinitrobenzene, 1,3,5-trintrobenzene, 2,3,7-trinitrofluorenone, benzophenone, naphthalene; lithium complex with the following: biphenyl, di-tert-butylbiphenyl, dimethylaminonaphthalene, trimesityl borane, di-tertbutylnaphthalene; lithium, sodium, potassium or calcium dissolved with ammonia, hexamethyl phosphoric triamide, 18-crown-6 or tris(3,6-dioxaheptyl)amine; magnesium, lithium; or n-butyllithium when $X_5$ is -I. It is preferred that the Type A reducing agent be lithium or sodium naphthalenide, lithium and sodium anthracene, lithium biphenyl, lithium di-tert-butylbiphenyl, lithium dimethylaminonaphthalene, lithium trimesityl borane, lithium di-tert-butylnaphthalene, lithium, sodium, potassium or calcium dissolved with ammonia, hexamethyl phosphoric triamide, 18-crown-6 or tris(3,6-dioxaheptyl)amine; magnesium; n-butyllithium when $X_5$ is -I. It is more preferred the Type A reducing agent be lithium biphenyl, sodium or lithium naphthalide or lithium 4,4'-di-tert-butylbiphenyl. It is preferred that about 2.2 to about 5 equivalents, more preferably about 2.5 to about 3 equivalents of the Type A reducing agent be used. Equivalents refers to the number of equivalents of electrons donated by the reducing agent. Any remaining Type A reducing agent is then destroyed with an aprotic quenching agent such as $\phi$-CH=$CX_{37}$-$X_{38}$ where $X_{37}$ and $X_{38}$ are the same or different and are $C_1$-$C_3$ alkyl or -$\phi$; $X_{31}X_{32}X_{33}$C-$CX_{34}X_{35}X_{36}$ where $X_{31}$, $X_{32}$, $X_{33}$, $X_{34}$, $X_{35}$ and $X_{36}$ are the same or different and are -H, -F, -Cl, -Br, -I, $C_1$-$C_7$ alkyl, $C_1$-$C_4$ halo alkyl where the halo atoms are -F, -Cl, -Br and -I; $X_{31}X_{32}X_{33}$C-CH=CH-$CX_{34}X_{35}X_{36}$; $X_{31}X_{32}$C=$CX_{34}$-$CX_{35}$=$CX_{35}X_{36}$ and benzoate. Preferred is dichloroethane, dibromoethane, and benzoate, more preferred is 1,2-dichloroethane. The purpose of the aprotic quenching agent is to remove excess Type A reducing agent from the reaction mixture before protons are added in the course of further processing. If protons are added prior to removal of the reducing agent, most of the reducing agents will produce significant (those included as Type B reducing agents) amounts of the corresponding progesterone (V) as a byproduct. Ideally, to produce only the 17-hydroxyprogesterone (VI), either a Type A-non-Type B reducing agent (such as magnesium) can be used, or the amount of Type A reducing agent can be limited to be just sufficient to consume the starting α-halo silyl ether (II). In practice, it is often easier and preferred to use an excess of the Type A reducing agent, then destroy the excess Type A reducing agent with the aprotic quenching agent. Suitable solvents include THF, dimethoxyethane alone or mixed with non-reactive solvents such as hexanes, heptanes, octanes, toluene, methyl-tert-butylether and mixtures thereof. Preferred is THF. The contacting is performed at about $-80°$ to about $20°$, preferably about $-20°$ to about $0°$, more preferably about $-10°$ depending on the particular reducing agent and particular α-substituted silyl ether (II). As is known to those skilled in the art for a particular situation the reducing agent and silyl ether (II) are contacted at a low temperature and the mixture is warmed until reaction occurs as measured by TLC. In that way one obtains the desired reaction using the minimum amount of heat. The reaction is complete (contacting time) in less than one minute or over twenty hours depending on the particular silyl ether (II), the solvent, the temperature, etc as is known to those skilled in the art. Usually the reaction is complete in a short time, for example in about 1 to about 5 minutes. The aprotic quenching agent is added until the reducing agent disappears. The reaction mixture is then quenched and hydrolyzed in the same manner and same way using the same reagents as described above for the 21-halo corticoids (III).

The α-halo silyl ether (II) can also be transformed to the 21-halo corticoid (III) by a similar procedure if both $X_3$ and $X_5$ are not H, see EXAMPLE 78.

The α-halo silyl ether (II) can be transformed to the corresponding progesterone (V) by contacting it with with an effective amount of a Type B reducing agent in the presence of one or more equivalents of protons followed by reaction with a protiodesilation reagent and a nitrogen to oxygen exchange reagent. An effective amount of a Type B reducing agent requires at least 4 equivalents, preferably about 4.5 to about 6 equivalents are used. Examples of Type B reducing agents include lithium and sodium complex of the following anthracene, naphthacene, benzanthracene, 20-methylcholanthrene, nitrobenzene, meta-dinitrobenzene, 1,3,5-trintrobenzene, 2,3,7-trinitrofluorenone, benzophenone, naphthalene; lithium complex of the following biphenyl, di-tert-butylbiphenyl, dimethylaminonaphthalene, trimesityl borane, di-tertbutylnaphthalene; lithium, sodium, potassium or calcium dissolved with ammonia, hexamethyl phosphoric triamide, 18-crown-6 or tris(3,6-dioxaheptyl)amine. Preferred are lithium or sodium naphthalenide, lithium and sodium anthracene, lithium biphenyl, lithium di-tert-butylbiphenyl, lithium dimethylaminonaphthalene, lithium trimesityl borane, lithium di-tert-butylnaphthalene, lithium, sodium, potassium or calcium dissolved with ammonia, hexamethyl phosphoric triamide, 18-crown-6 or tris(3,6-dioxaheptyl)amine, more preferred are lithium biphenyl, sodium or lithium naphthalide or lithium 4,4'-di-tert-butylbiphenyl. Alternatively, treatment of the silyl ether (II) with a Type A reducing agent followed by sufficient amount of Type B reducing agent is operable. It is preferred that the reducing agent used be all of of the Type B. In order to accomplish the reduction to progesterones (V) the contacting must take place in the presence of one or more equivalents of protons. Suitable proton sources include water, $R_{50}$-OH where $R_{50}$ is selected from the group consisting of $C_1$-$C_7$ alkyl, -$\phi$, -$CH_2$-$\phi$, -$CH_2CH_2$-$OCH_3$, HO-$R_{51}$-OH where $R_{51}$ is $C_2$-$C_7$ alkyl, propylene glycol, ethylene glycol, glycerol, acids selected from the group consisting of HF, HCl, HBr, HI, $H_3PO_4$, $H_2SO_4$, perchloric, fluoroboric, $NaHSO_4$, $NaH_2PO_4$, polymeric sulfonic acid cation exchange resins, HOOC-$(CH_2)_n$-COOH where n is 0 through 12, tartaric acid, citric acid, $B(X_{19})_3$, $Al(X_{19})_4$, $Sn(X_{19})_4$, $Sn(X_{19})_2$ and $Ti(X_{19})_4$ where $X_{19}$ is -F, -Cl, -Br and -I, $R_{52}$-COOH and $R_{52}$-$SO_3$-H where $R_{52}$ is -H, $C_1$-$C_{12}$ alkyl, -$\phi$, methylphenyl, -$CF_3$, -$CCl_3$; hydrochloride and hydrobromide salts of amines of the formula $NX_{12}X_{13}X_{14}$ where $X_{12}$, $X_{13}$ and $X_{14}$ the same or different and are -H, -φ, -CH$_2$-φ, -CH$_2$CH$_2$-φ, methylphenyl, C$_1$-C$_9$ alkyl optionally substituted with 1 or more oxygen or nitrogen atoms, the alkyl groups can be cyclized with the attached nitrogen atom and 1 or more oxygen or nitrogen atoms to form 1 through 3 rings with the proviso that at least 1 of X$_{12}$, X$_{13}$ and X$_{14}$ is -H and the steroid portion of the α-halo silyl ether (II) when it contains a free -OH group. Preferred proton sources are water and an acid. The α-halo silyl ether (II) itself can serve as the proton source, if it contains unprotected hydroxyl groups. The proton source may be added either with the α-halo silyl ether (II), or following the contacting between the α-halo silyl ehter (II) and the reducing agent. It is preferred to add the proton source following the contacting between the α-halo silyl ether (II) and the reducing agent. Suitable solvents include THF, dimethoxyethane and non-reactive solvents such as hexanes, heptanes, octanes, toluene, methyl-tert-butyl ether and mixtures thereof. Preferred is THF. The contacting is performed at about −80° to about 20°, preferably about −30° to about −10°, more preferably about −20°. The reaction is complete in less than one minute or over twenty hours depending on the particular silyl ether (II), the solvent, the temperature, etc as is known to those skilled in the art. Usually the reaction is complete in a short time about 1 to about 5 minutes. The reaction mixture is quenched and hydrolyzed in the same manner and the same way using the same reagents as described above for the 21-halo corticoids (III). For convenience, it is preferred that the proton source and the a protiodesilation reagent and a nitrogen to oxygen exchange reagent be the same, for example a mixture of aqueous hydrochloric or sulfuric acid in methanol or ethylene glycol.

Oxidative cleavage reactions of silicon-carbon bonds are known to those skilled in the art, see J. Org. Chem., 48, 2120 (1983), Tetrahedron Letters 25, 4245 (1984), J. Organometallic Chem., 269 (1984), Tetrahedron 39, 983 (1983) and Tetrahedron Letters 27, 75 (1986).

The α-halo silyl ether of formula II can be transformed directly to a corticoid (VII) by (1) contacting it with an effective amount of a Type A reducing agent, (2) contacting the mixture of step (1) with an oxidizing agent and (3) contacting the mixture of step (2) with a protiodesilation reagent and a nitrogen to oxygen exchange reagent. As exemplified in EXAMPLE 62, oxidative cleavage of a silicon-carbon bond following reaction of the α-halo silyl ether (II) with two or more equivalents of a Type A reducing agent and (optionally) an aprotic quenching agent gives corticoids (VII) directly. Suitable Type A reducing agents and aprotic quenching agents are set forth supra. Suitable oxidative agents include hydrogen peroxide, t-butyl hydroperoxide, peracetic acid, perbenzoic acid, m-chloroperbenzoic acid, perphthalic acid, trifluoroperacetic acid, cumyl hydroperoxide, trimethylamine-N-oxide, acetone hydroperoxide, hexafluroacetone hydroperoxide, N-phenylsulfonyl-3-phenyloxaziridine and m-chloroperbenzoic acid, preferred are hydrogen peroxide, m-chloroperbenzoic acid and trimethylamine-N-oxide. Salts of the oxidizing agents are equivalent to the free oxidizing agents. The reaction mixture is quenched and hydrolyzed in the same manner and the same way using the same reagents as described above for the 21-halo corticoids (III).

The difference between the process to the progesterones (V) and 17-hydroxyprogesterones (VI) from the α-halo silyl ether (II) is, with regard to the progesterones (V), at least 4 equivalents of the reducing agent are required and at least 1 equivalent of a proton source must be present during the contacting of step (1). With the process to the 17-hydroxyprogesterones (VI) only 2 equivalents of the Type A reducing agent are required and an aprotic quenching agent may be used. For instance, with the process to the 17-hydroxyprogesterones (VI), 4 equivalents of the Type A reducing agent can be used (preferably not), if no proton source is present and the quenching agent is an aprotic quenching agent.

It is important that the α-halo silyl ether (II) have any reducible functional groups present protected, if it is desired that they not be reduced. Reducible functional groups include enones, ketones and halides, depending on the reducing agent. Enones are protected as the ketal or dienol ether or dienolate, as is known to those skilled in the art, if it is desired not to have such functional groups reduced by the reducing agent.

For the production of the 21-halo corticoids (III), progesterones (V) and 17-hydroxyprogesterones (VI) it is important that the reactions and quenches be conducted in an inert atmosphere, preferably of nitrogen or argon, most preferably of argon.

The compounds of the present invention (I–III, V and VI) have an asymmetric center at C$_{17}$. Because of the planar nature of the steroid ring system the two substituents at C$_{17}$ have a relationship to each other of above and below the plane of the steroid ring system which is denoted as α (below) and β (above) configuration by those skilled in the art. While the chemical formulas set forth in CHARTS A thru D (and the claims) show the normal configuration for the formulas set forth, these formulas are meant to disclose and include the epi configuration as well. For example, with the cyanohydrin (I), the normal configuration is that set forth in formula (I), 17β-cyano-17α-hydroxy. However, this formula by definition is meant to, and does, include the epi configuration for the cyanohydrin (I) which is 17α-cyano-17β-hydroxy. Likewise for the steroids (II, III and VI).

Although the 17β-hydroxy steroids are not generally utilized as pharmaceutical agents and thus fewer of them are known and described than the 17α-hydroxy steroids, they can be useful intermediates in the production of pharmaceuticals. EXAMPLE 40 describes the preparation of a 21-chloro-17β-hydroxypregnane and its conversion to a useful melengestrol acetate precursor (U.S. Pat. No. 4,567,001). EXAMPLES 54–56 describe the prepartion of a precursor for 17-epi hydrocortisone, useful as an analytical standard for determining the level of this impurity in hydrocortisone.

DEFINITIONS

The definitions and explanations below are for the terms as used throughout this entire document including both the specification and the claims.

All temperatures are in degrees Centigrade.

TLC refers to thin-layer chromatography.

HPLC refers to high pressure liquid chromatography; which was performed on a C-18 250 cm column, at 20°–25° with 1 ml/min, 30 min, eluting with water/acetonitrile/methanol (40/40/20) using a gradient to acetonitrile/methanol (70/30).

LDA refers to lithium diisopropylamide; [for metal-N(X$_7$) (X$_8$) metal is lithium, X$_7$ and X$_8$ are isopropyl].

LiHMDS refers to lithium bis(trimethylsilyl)amide

THF refers to tetrahydrofuran.

DMF refers to dimethylformamide.

TEA refers to triethylamine.

NMR refers to nuclear (proton) magnetic resonance spectroscopy, chemical shifts are reported in ppm (δ) downfield from tetramethylsilane.

TMS refers to trimethylsilyl. φ refers to phenyl ($C_6H_5$).

When solvent pairs are used, the ratios of solvents used are volume/volume (v/v).

Medroxyprogesterone acetate refers to 17α-hydroxy-6α-methylpregn-4-ene-3,20-dione 17-acetate.

THF refers to tetrahydrofuran.

p-TSA refers to p-toluenesulfonic acid monohydrate.

Saline refers to an aqueous saturated sodium chloride solution.

Ether refers to diethyl ether.

EXAMPLES

Without further elaboration, it is believed that one skilled in the art can, using the preceding description, practice the present invention to its fullest extent. The following detailed examples describe how to prepare the various compounds and/or perform the various processes of the invention and are to be construed as merely illustrative, and not limitations of the preceding disclosure in any way whatsoever. Those skilled in the art will promptly recognize appropriate variations from the procedures both as to reactants and as to reaction conditions and techniques.

PREPARATION 1

17β-Cyano-3,17α-dihydroxyandrosta-3,5,9(11)-triene 3-methyl ether (I)

Following the general procedure of U.S. Pat. No. 4,548,748, Example 214, and making non-critical variations but starting with 17β-cyano-17α-hydroxyandrosta-4,9(11)-dien-3-one (U.S. Pat. No. 4,548,748, Example 2), the title compound is obtained.

PREPARATION 2

17β-Cyano-3,11β,17α-trihydroxyandrosta-3,5-diene 3-ethyl ether (I)

17β-Cyano-11β,17α-dihydroxyandrost-4-en-3-one (1.5793 g), toluene (4.7 ml), ethanol (1.6 ml), triethylorthoformate (0.44 eq), pyridine hydrochloride (0.6 eq) and formic acid (0.11 eq) are combined and heated to 55° and stirred. Additional triethylorthoformate is added. Additional ethanol is added to solubilize everything. When the reaction is complete as determined by TLC (ethyl acetate/hexane, 1/1) the mixture is distilled under reduced pressure adding TEA and hexane. After sitting solids precipitate. The mixtue is filtered and the solids are washed. The filtrate is concentrated to an oil (after more solids are filtered off) to give the title compound.

PREPARATION 3

17β-Cyano-11β,17α-dihydroxy-6α-methylandrost-4-en-3-one (I)

Following the general procedure of PREPARATION 1 and making non-critical variations but starting with 11β-hydroxy-6α-methylandrost-4-ene-3,17-dione (0), the title compound is obtained, m.p. 215.3°–217.5°; NMR ($CD_2Cl_2/CD_3OD$) 1.0, 1.2, 1.5, 4.5 and 5.7 δ.

PREPARATION 4

17β-Cyano-11β,17α-dihydroxy-6α-methylandrosta-1,4-dien-3-one (I)

Glacial acetic acid (0.050 ml) is added to 11β-hydroxy-6α-methylandrosta-1,4-dien-3,17-dione (0, 236.4 mg), potassium cyanide (97.47 mg) in methanol (0.396 ml) and water (0.264 ml) and the mixture stirred at 20°–25°. Initially, a single product forms by TLC which is gradually replaced by a second product over the course of the reaction. When this conversion is complete as measured by TLC, glacial acetic acid (0.0606 ml) is added. The reaction mixture is dissolved in a minimal amount of methanol, water and methylene chloride. The mixture is concentrated under reduced pressure until crystallization of the product appears complete. The slurry is filtered, and the crystals washed with several portions (1 ml) of methanol/water (1/1). The crystals are triturated with ethyl acetate acidified with acetic acid, filtered and dried under reduced pressure at 45° overnight to give the title compound, m.p. 257.7°–258.9°; NMR ($DMSO-d_6$) 1.0, 1.1, 1.4, 4.3, 4.8, 5.8, 6.1, 6.2 and 7.3 δ.

PREPARATION 5

17β-Cyano-6-fluoro-3,17α-dihydroxyandrosta-3,5,9(11)-triene 3-methyl ether (I)

Glacial acetic acid (0.61 ml) is added to 6α-fluoro-3-hydroxy-androsta-3,5,9(11)-trien-17-one 3-methyl ether (0, 1.647 g), potassium cyanide (1.126 g) slurried in THF (1.4 ml) and methanol (4.1 ml) under nitrogen at 42°. After 15 min water (1.4 ml) is added dropwise over 1 minute maintaining the temperature between 29° and 35°. After 45 min, seed crystals of the title compound are added. Initially, a single product forms by TLC which is gradually replaced by a second product over the course of the reaction. When this conversion is complete, glacial acetic acid (0.38 ml) is added and the mixture is cooled to 20°–25°. The resultant crystals are collected by vacuum filtration, washed with methanol/water (1/1, 2×10 ml), and dried at 50° under vacuum for 6 hrs to give the title compound, m.p. 167°–172°; NMR ($CDCl_3$) 0.9, 1.1, 3.6, 5.5 and 5.6 δ.

PREPARATION 6

17β-Cyano-6α-fluoro-17α-hydroxyandrosta-4,9(11)-dien-3-one (I)

To 17β-cyano-6-fluoro-3,17α-dihydroxyandrosta-3,5,9(11)-triene 3-methyl ether (PREPARATION 5, 196.8 mg), glacial acetic acid (1.00 ml), water (0.10 ml), then p-TSA monohydrate (23.3 mg) is added. The mixture is stirred at 20°–25° for 17 min then poured into a mixture of aqueous potassium phosphate monobasic (20 ml) and methylene chloride (20 ml). The phases are separated and the aqueous layer washed with methylene chloride (5 ml). The combined organic layers are washed with water (10 ml) and dried on anhydrous sodium sulphate. The mixture is concentrated under reduced pressure to an oil. Column chromatography eluting with ethyl acetate/hexane (30/70) gives the title compound, m.p. 222° (dec); NMR ($CDCl_3/CD_3OD$) 0.8, 1.3, 5.7 and 6.0 δ.

PREPARATION 7

17α-Cyano-17β-hydroxy-16-methyleneandrost-4-en-3-one (I)

Trimethylsilylcyanide (4.7 ml) and 18-crown-6/potassium cyanide complex (0.211 g) are added to a solution of 3-hydroxy-16-methyleneandrosta-3,5-dien-17-one 3-methyl ether (0, U.S. Pat. No. 4,416,821 Example 8, 10 g) in methylene chloride (50 ml). The mixture is stirred for 1 hr. Methanol (50 ml) and hydrofluoric acid (48%, 10 ml) are added and the mixture is stirred for 2.5 hr then partitioned between methylene chloride and saline. The aqueous layer is extracted with methylene chloride. The organic extracts are washed with saline, dried over sodium sulfate and concentrated to a crystalline product which is recrystallized from isopropanol to give the title compound, NMR (CD$_2$Cl$_2$) 5.30, 5.51 and 5.69 δ.

PREPARATION 8

17β-Cyano-11β,17α-dihydroxy-6-methyleneandrost-4-en-3-one (I)

Following the general procedure of PREPARATION 3 and making non-critical variations but starting with 11β-hydroxy-6-methylenandrost-4-ene-3,17-dione (0) the title compound is obtained, m.p. 245°–255°; NMR (CDCl$_3$/DMSO-d$_6$) 1.1, 1.2, 4.3, 4.5, 5.0, 5.7, and 6.3 δ.

PREPARATION 9

17α-Cyano-17β-hydroxyandrosta-4,9(11)-dien-3-one (I)

Following the general procedure of PREPARATION 7 and making non-critical variations but starting with 3-hydroxyandrosta-3,5,9(11)-trien-17-one 3-methyl ether (0, U.S. Pat. No. 3,516,991), the title compound is obtained.

PREPARATION 10

17β-Cyano-17α-hydroxyandrosta-5,9(11)-diene 3-ethylene ketal (I)

Following the general procedure of EXAMPLE 59 and making non-critical variations but starting with androsta-5,9(11)-dien-17-one 3-ethylene ketal (0), the title compound is obtained.

EXAMPLE 1

17β-Cyano-17α-hydroxyandrosta-4,9(11)-dien-3-one 17-(chloromethyl)dimethylsilyl ether (II)

17β-Cyano-17α-hydroxyandrosta-4,9(11)-dien-3-one (I, EXAMPLE 86, 75.03 g) is mixed with methylene chloride (150 ml). Atmospherically, 75 ml of the methylene chloride is distilled off and the procedure is repeated. The mixture is then cooled to −4°. A mixture of 4-dimethylaminopyridine (0.6358 g) in methylene chloride (10 ml) is added to the steroid mixture. This is followed by addition of triethylamine (44 ml) over 3 min maintaining the temperature <5°. Chloromethyldimethylchlorosilane (38.8 ml) is added from an additional funnel maintaining the temperature <0°. The mixture is stirred until the reaction is complete as measured by TLC. The reaction mixture is then added via a cannula to a mixture of aqueous potassium phosphate monobasic (243 ml) and methylene chloride (75 ml) which had been previously cooled to 2° with vigorous stirring. The reaction mixture flask is rinsed with methylene chloride, stirring is stopped and the layers separated. The aqueous layer is washed with methylene chloride (3×50 ml) and the organic phases are combined. The organic phase is backwashed with water (300 ml). Each aqueous backwash is in turn backwashed in order with a mixture of iso-octanes (75 ml). The iso-octane layer is combined with the previous organic layers. The mixture is concentrated under reduced pressure while adding iso-octane. Distillation is stopped when the vapor temperature is about 38°. The slurry is cooled and filtered. The solids are dried under reduced pressure at about 50° to give the title compound, m.p. 138°–141°; NMR (CDCl$_3$) 0.9, 1.0, 1.2, 3.9 and 5.7 δ.

EXAMPLE 2

17β-Cyano-17α-hydroxyandrosta-4,9(11)-dien-3-one 17-(bromomethyl)dimethylsilyl ether (II)

Following the general procedure of EXAMPLE 1 and making non-critical variations but using bromomethyldimethylchlorosilane, the title compound is obtained.

EXAMPLE 3

17β-Cyano-3,17α-dihydroxyandrosta-3,5,9(11)-triene 3-methyl ether 17-(chloromethyl)dimethylsilyl ether (II)

Triethylamine (70.82 g) is added dropwise over a period of 5 minutes to a suspension of 17β-cyano-3,17α-dihydroxyandrosta-3,5,9(11)-triene 3-methyl ether (PREPARATION 1, 168.38 g), 4-dimethylaminopyridine (3.1562 g) and methylene chloride (860 ml) at 1° under nitrogen maintaining the temperature at about 1°. Chloromethyldimethylsilyl chloride (91.78 g) is added dropwise over 11 min with the temperature rising to 10°. Methylene chloride (10 ml) is used as a rinse. The reaction mixture is poured into phosphate buffer (1.5M potassium dihydrogen phosphate/sodium hydroxide to pH 7, 860 ml) containing ice (about 700 g). The mixture is stirred vigorously for about 10 min with the pH remaining at 7.5. The mixture is extracted with methylene chloride (3×500 ml). An intermediate layer is formed. It is filtered. The resulting solid is washed with water, then with methylene chloride. The combined methylene chloride layers are dried over magnesium sulfate, filtered, and the filtrate concentrated to about 800 ml. This filtrate is warmed under reduced pressure to remove the methylene chloride. As methylene chloride is removed, heptane (650 ml) is added to maintain a reasonably constant volume. Crystals begin to form after about 500 ml of heptane has been added. After all the heptane is added the mixture is warmed to 30° for 10 min to remove the remaining methylene chloride. The mixture is cooled to 0° and held for 15 min. The resulting solid is filtered and washed with heptane (3×100 ml), dried at 20°–25° to constant weight to give the title compound. The filtrate is concentrated to a mushy solid residue using heat (40°) and reduced pressure overnight. The mixture is triturated with heptane and filtered, the solid is washed with heptane (2×20 ml) to obtain additional title compound, m.p. 145°–153°; NMR (CDCl$_3$) 0.4, 0.9, 1.2, 2.9, 3.6, 5.2 and 5.3 δ.

EXAMPLE 4

21-Chloro-17α-hydroxypregna-4,9(11)-diene-3,20-dione (III)

17β-Cyano-3,17α-dihydroxyandrosta-3,5,9(11)-triene 3-methyl ether 17-(chloromethyl)dimethylsilyl ether (II, EXAMPLE 3, 10.8 g) and dry THF (34.8 ml), are cooled to −40°. LDA [1.94 molar bis(tetrahydrofuran complex) in a mixture of iso-octanes, 19.3 ml] is added dropwise with stirring over 6 minutes maintaining the temperature at < −18°. After ½ hr the reaction is quenched by adding the reaction mixture to a mixture of concentrated hydrochloric acid (25 ml) and ethylene glycol (4.2 ml) at −30°. The reaction mixture is stirred at about −30° to about 25° for about 3.5 hr, iso-octane (70 ml) is added over 5 minutes followed by the addition of water (225 ml) over about 10 minutes. The reaction mixture is filtered, washed with water followed by iso-octane and the dried overnight at about 45° to give the title compound.

EXAMPLE 5

21-Chloro-17α-hydroxypregna-4,9(11)-diene-3,20-dione (III)

17β-Cyano-17α-hydroxyandrosta-4,9(11)-dien-3-one 17-(chloromethyl)dimethylsilyl ether (II, EXAMPLE 1, 10.4541 g) and dry THF (35 ml) are cooled to −39°. Chlorotrimethylsilane (2.7 ml) is added followed by a nitrogen flush. LDA [1.94 molar bis(tetrahydrofuran complex) in a mixture of iso-octanes, 32.2 ml] is added dropwise with stirring maintaining the temperature < −30°. The reaction mixture is then cooled to −57° and stirred for an additional hour. LDA (1.8 ml) is then added permitting the temperature to rise to −26°. The reaction mixture is then added to concentrated hydrochloric acid (30 ml) and ethylene glycol (4.2 ml). THF/iso-octanes (1/1, 20 ml) is washed into the mixture and the temperature is permitted to rise to 8°. When the reaction is complete, as monitored by HPLC, iso-octanes (70 ml) is added dropwise over about 10 mi followed by addition of water (225 ml). The reaction mixture is filtered, washed with water/iso-octanes dried under reduced pressure with heat to give the title compound, NMR (CDCl$_3$-CD$_3$OD) 0.5, 1.2, 4.4, 5.4 and 5.6 δ.

EXAMPLE 6

21-Bromo-17α-hydroxypregna-4,9(11)-diene-3,20-dione (III)

Following the general procedures of EXAMPLES 4 and 5, and making non-critical variations but starting with 17β-cyano-17α-hydroxyandrosta-4,9(11)-dien-3-one 17-(bromomethyl)dimethylsilyl ether (II, EXAMPLE 2), the title compound is obtained.

EXAMPLE 7

17β-Cyano-17α-hydroxyandrosta-1,4,9(11)-trien-3-one 17-(chloromethyl)dimethylsilyl ether (II)

Following the general procedure of EXAMPLES 1 and 3 and making non-critical variations but starting with 17β-cyano-17α-hydroxyandrosta-1,4,9(11)-trien-3-one, the title compound is obtained, m.p. 170.5°–172°; NMR (CDCl$_3$) 0.5, 1.3, 4.4, 5.5, 6.0, 6.2 and 7.1 δ.

EXAMPLE 8

17β-Cyano-17α-hydroxyandrost-4-en-3-one 17-(bromomethyl)dimethylsilyl ether (II)

Following the general procedure of EXAMPLE 2 and making non-critical variations but starting with 17β-cyano-17α-hydroxyandrost-4-en-3-one (U.S. Pat. No. 4,500,461, Example 1) and bromomethyldimethylchlorosilane, the title compound is obtained, m.p. 133°–136°; NMR (CDCl$_3$) 0.4, 0.9, 1.2, 2.5, and 5.7 δ.

EXAMPLE 9

17β-Cyano-17α-hydroxyandrost-5-en-3-one 3-ethylene ketal 17-(chloromethyl)dimethylsilyl ether (II)

Following the general procedure of EXAMPLES 1 and 3 and making non-critical variations but starting with 17β-cyano-17α-hydroxyandrost-5-en-3-one 3-ethylene ketal (U.S. Pat. No. 4,500,461, Example 3), the title compound is obtained, m.p. 135°–136°.

EXAMPLE 10

17β-Cyano-3-ethoxy-17α-hydroxyandrosta-3,5,9(11)-triene 17-(chloromethyl)dimethylsilyl ether (II)

Following the general procedure of EXAMPLES 1 and 3 and making non-critical variations but starting with 17β-cyano-3-ethoxy-17α-hydroxyandrosta-3,5,9(11)-triene, the title compound is obtained, m.p. 111°–118°.

EXAMPLE 11

17β-Cyano-17α-hydroxyandrost-4-en-3-one 17-(chloromethyl)dimethylsilyl ether (II)

Following the general procedure of EXAMPLES 1 and 3 and making non-critical variations but starting with 17β-cyano-17α-hydroxyandrost-4-en-3-one (U.S. Pat. No. 4,500,461, Example 1), the title compound is obtained, m.p. 143°–146°.

EXAMPLE 12

17β-Cyano-3,17α-dihydroxyandrosta-3,5-diene 3-methyl ether 17-(chloromethyl)dimethylsilyl ether (II)

Following the general procedure of EXAMPLES 1 and 3 and making non-critical variations but starting with 17β-cyano-17α-hydroxy-3-hydroxyandrosta-3,5-diene 3-methyl ether, the title compound is obtained, m.p. 117°–120°.

EXAMPLE 13

17β-Cyano-3,17α-dihydroxyandrosta-3,5-diene 3-methyl ether 17-(bromomethyl)dimethylsilyl ether (II)

Following the general procedure of EXAMPLES 1 and 3 and making non-critical variations but starting with 17β-cyano-17α-hydroxy-3-hydroxyandrosta-3,5-diene 3-methyl ether and bromomethyldimethylchlorosilane, the title compound is obtained, m.p. 122°–130°; NMR (CDCl$_3$) 0.4, 0.5, 1.0, 2.1, 3.5, 5.1 and 5.2 δ.

EXAMPLE 14

21-Chloro and 21-Bromo Corticoids (III)

Following the general procedure of EXAMPLES 4, 5 and 6 and making non-critical variations but starting with the α-halo silyl ethers (II) of EXAMPLES 7 through 13, the corresponding 21-chloro and 21-bromo corticoids (III) are obtained.

EXAMPLE 15

17β-Cyano-17α-hydroxy-16β-methylandrosta-1,4,9(11)-trien-3-one (I)

16β-Methylandrosta-1,4,9(11)-triene-3,17-dione (U.S. Pat. No. 3,010,958, 12.0 g) and potassium cyanide (7.909 g) are suspended in methanol (24 ml). The resulting slurry is then treated with glacial acetic acid (3.5 ml) and allowed to stir in a tightly stoppered flask at 20°–25° for 72 hr. TLC (acetone/methylene chloride, 4/96). The reaction mixture is then cooled to 0° and quenched with glacial acetic acid (4.2 ml). The solids are then collected by filtration, triturated with methanol/water (1/1, 3×10 ml) and dried by heating (60°) under reduced pressure (60 mm) to obtain the title compound, m.p. 241°–247.5°; NMR ($CD_2Cl_2$) 1.32, 1.42, 5.58, 6.08, 6.30 and 7.25 δ.

EXAMPLE 16

17β-Cyano-17α-hydroxy-16β-methylandrosta-1,4,9(11)-trien-3-one 17-(chloromethyl)dimethylsilyl ether (II)

Following the general procedure of EXAMPLES 1 and 3 and making non-critical variations but starting with 17β-cyano-17α-hydroxy-16β-methylandrosta-1,4,9(11)-trien-3-one (I, EXAMPLE 15) the title compound is obtained, NMR ($CDCl_3$) 0.30, 0.30, 0.91, 1.27, 1.38, 2.81, 5.55, 6.02, 6.24 and 7.17 δ.

EXAMPLE 17

21-Chloro-17α-hydroxy-16β-methylpregna-1,4,9(11)-triene-3,20-dione (III)

17β-Cyano-17α-hydroxy-16β-methylandrosta-1,4,9(11)-trien-3-one 17-(chloromethyl)dimethylsilyl ether (II, EXAMPLE 16, 0.213 g) is dissolved in THF (3.0 ml). The resulting mixture is coolded to −30°, then treated with a mixture of lithium hexamethyldisilazide (0.71 mmoles) in THF (2.0 ml). The resulting mixture is stirred at −30° for 5 min, then treated with a mixture of trimethylchlorosilane (45 mg) in THF (1.0 ml). The resulting mixture is stirred at −30° for 10 min, then treated with a mixture of LDA bis(tetrahydrofuran)-complex in a mixture of iso-octanes (2.02M, 0.95 ml). The resulting mixture is stirred at −20° for 50 min, at which time all of the starting material had been consumed according to TLC (ethyl acetate/cyclohexane, 30/70). The reaction mixture is added to a polyethylene bottle containing aqueous hydrofluoric acid (48%, 1.6 ml). The mixture is stirred under argon at 20°–25° for 23 hr, then poured into water (100 ml), extracted with methylene chloride (6×20 ml). The combined extracts are dried over anhydrous magnesium sulfate and concentrated to give the title compound, NMR ($CDCl_3$) 0.85, 1.11, 1.42, 4.42, 4.69, 5.55, 6.07, 6.27, and 7.25 δ.

EXAMPLE 18

17α,21-Dihydroxy-16β-methylpregna-1,4,9(11)-triene-3,20-dione 21-acetate (VII)

21-Chloro-17α-hydroxy-16β-methylpregna-1,4,9(11)-triene-3,20-dione (III, EXAMPLE 17, 0.151 g), potassium acetate (0.099 g), tributylmethylammonium chloride (0.014 g), acetic acid (0.010 g) and water are dissolved in methylene chloride (1.0 ml) and acetone (2.5 ml). The mixture is stirred at 55° for 17 hr at which time the conversion of starting material into product is complete (TLC-silica gel, acetone/methylene chloride, 10/90). The reaction mixture is poured in aqueous hydrochloric acid (5%, 50 ml) and extracted with methylene chloride (3×15 ml). The combined extracts are dried over anhydrous magnesium sulfate and concentrated to give the title compound, NMR ($CD_2Cl_2$) 0.74, 1.09, 1.38, 2.11, 4.88, 4.97, 5.54, 5.98, 6.20 and 7.23 δ.

EXAMPLE 19

17β-Cyano-17α-hydroxyandrosta-1,5,9(11)-trien-3-one 17-(chloromethyl)dimethylsilyl ether (II)

A mixture of lithium bis(trimethylsilyl)amide is added to 17β-cyano-17α-hydroxyandrosta-1,4,9(11)-trien-3-one 17-(chloromethyl)dimethylsilyl ether (II, EXAMPLE 7, 2.987 g) in dry THF (15 ml) stirring at −50° over a period of 4 minutes. The mixture is warmed to 15° and stirred for 36 min. The mixture is quenched by adding to ammonium chloride buffer and pentane. Extraction from the buffer mixture gives the title compound, NMR ($CDCl_3$) 0.4, 0.9, 1.4, 2.8, 5.5, 5.8, 5.9 and 7.3 δ.

EXAMPLE 20

17β-Cyano-3,17α-dihydroxyandrosta-1,4,9(11)-triene 3-trimethylsilyloxy ether 17-(chloromethyl)dimethylsilyl ether (II)

Chlorotrimethylsilane (0.73 ml) is added to 17β-cyano-17α-hydroxyandrosta-4,9(11)-dien-3-one 17-(chloromethyl)dimethylsilyl ether (II, EXAMPLE 1, 3.0061 g) in dry THF (7.0 ml) stirred at −20°. This is followed by dropwise addition of bis(trimethylsilyl)amine (0.3 ml), then LDA (1.99M bis(tetrahydrofuran) in a mixture of iso-octane, 3.6 ml). The mixture is quenched by adding to ammonium chloride buffer (2M) and pentane. Extraction from the buffer mixture gives the title compound, NMR ($CDCl_3$) 0.4, 0.9, 1.1, 2.9, 4.8, 5.3 and 5.4 δ.

EXAMPLE 21

17β-Cyano-3-ethoxy-17α-hydroxyandrosta-3,5-diene 17-(chloromethyl)dimethylsilyl ether (II)

Following the general procedure of EXAMPLES 1 and 3 and making non-critical variations but starting with 17β-cyano-3-hydroxy-17α-hydroxyandrosta-3,5-diene 3-ethyl ether (I) and chloroethyldimethylchlorosilane, the title compound is obtained, NMR ($CDCl_3$) 0.4, 0.9, 1.0, 1.3, 2.9, 3.8 and 5.2 δ.

EXAMPLE 22

21-Chloro-17α-hydroxypregna-1,4,9(11)-triene-3,20-dione (III)

Following the general procedure of EXAMPLE 17 and making non-critical variations but starting with 17β-cyano-17α-hydroxyandrosta-1,4,9(11)-trien-3-one 17-(chloromethyl)dimethylsilyl ether (II, EXAMPLE 7), the title compound is obtained, m.p. 205°–206°.

EXAMPLE 23

Progesterone (V)

17β-Cyano-3-ethoxy-17α-hydroxyandrosta-3,5-diene 17-(chloromethyl)dimethylsilyl ether (II, EXAMPLE 21, 7.21 g) is dissolved in dry THF (17.5 ml). This mixture is added to a solution of lithium biphenyl (0.097 moles) in THF (0.2M) over 9 minutes at −20°. The funnel is rinces with THF (5 ml). Once the addition is complete a solution of sulfuric acid (6M, 72 ml) in methanol (36 ml) is added over a period of one minute. The −20° bath is replaces with an ice bath and the reaction is allowed to warm to 20°–25° and stirred until the reaction is complete as measured by TLC. Additional methanol is added to dissolve the solids and water (25 ml) is added. The reaction is concentrated to a low volume, filtered, washed with water until the filtrate is no longer acidic. The solids are dissolved in methylene chloride and chromatographed on a column. The column is eluted with ethyl acetate (10→30%) in methylene chloride. The appropriate fractions are pooled and concentrated to give the title compound, which is consistent with a known sample, TLC (acetone/methylene chloride, 5/95) $R_f$=0.75.

EXAMPLE 24

17α-hydroxyprogesterone (VI)

17β-Cyano-3,17α-dihydroxyandrosta-3,5-diene 3-methyl ether 17-(chloromethyl)dimethylsilyl ether (II, EXAMPLE 12, 2.98 g) in dry THF (5 ml). This solution is then added to a solution of lithium naphthalenide (21.1 mmol, 0.5M in THF) that has been cooled to −78°. The steroid solution is added dropwise but very fast. The syringe is rinsed with THF (2.4 ml). Sufficient dichloromethane (0.25 ml) is added quickly dropwise. The total time from the begining of the addition of the silyl ether (II) to the quenching with methylene chloride is 9 min. The reaction mixture is stirred 4 min. Hydrochloric acid (21.0 ml) is added over 5 minutes; the first half is added more slowly than the last half. When the acid quench is complete, the reaction mixture is removed from the dry ice acetone bath, methanol (21 ml) is added and the reaction mixture is permitted to warm to 20°–25°. Once the reaction is complete as measured by TLC (acetone/methylene chloride: 5/95), the mixture is concentrated on a rotory evaporatory to remove the solvents, cooled, filtered, the cake is washed with water until the filtrate is no longer acidic. The solid is dried under reduced pressure for 2 hr. The solid is then slurried in a mixture of iso-octanes (20 ml) at 54°–60° for 35 min. The hot slurry is filterd, the solids are washed with hot iso-octanes (3×4 ml) and dried to give the title compound, which is consistent with a known sample, TLC (acetone/methylene chloride, 5/95) $R_f$=0.25; HPLC retention time=10.63 min.

EXAMPLE 25

17β-Cyano-11β,17α-dihydroxyandrost-4-en-3-one 17-(chloromethyl)dimethylsilyl ether (II)

17β-Cyano-11β,17α-dihydroxyandrost-4-en-3-one (U.S. Pat. No. 4,585,590, Example 25, 6.28 g) and imidazole (1.82 g) are suspended in methylene chloride (20 ml) and cooled to 0°. Chloro(chloromethyl)dimethylsilane is added dropwise and the resulting mixture is stirred for 15 min at 0°. The reaction is quenched by adding saturated sodium bicarbonate (1 ml), resulting in two liquid phases. The phases are separated. The aqueous phases is extracted with methylene chloride (7 ml), the organic phases are combined and distilled atmospherically. After most of the solvent is removed, additional methanol is added (10 ml) and the distillation is continued. Again, after most of the solvent is removed methanol (10 ml) and water (10 ml) are added. The mixture is cooled to 20°–25° and filtered. The solids are washed with cold (0°) aqueous methanol (33% aqueous), dried at 45° under reduced pressure (27" Hg) for several hours to give the title compound, m.p. 258°–262° (dec); NMR (CDCl$_3$) 0.3, 1.2, 1.4, 2.8, 4.4 and 5.6 δ.

EXAMPLE 26

21-Chloro-11β,17α-dihydroxypregn-4-ene-3,20-dione (III)

17β-Cyano-11β,17α-dihydroxyandrost-4-en-3-one 17-(chloromethyl)dimethylsilyl ether (II, EXAMPLE 25, 1.032 g) is suspended in THF (6 ml). The slurry is cooled to −45° and trimethylsilyl chloride (0.24 ml) is added. The flask is flushed with nitrogen and LDA (1.5M in chclohexane, 6 ml, 3.8 equivalents) is added dropwise to the slurry over a period of 5 min maintaining the temperature below-35°. The reaction is then permitted to warm up to −20°. After one hour at −20°, the mixture is cooled to −78° and transferred to a flask containing ethylene glycol (0.5 ml) and hydrochloric acid (12M, 6 ml) cooled to −45°. The mixture is stirred for 1 hr while warming to 20°–25°. The mixture is then distilled under reduced pressure at 20°, until 5 ml of distillate is collected. Water (5 ml) is then slowly added. The slurry is stirred at 20°–25° for 10 min, then cooled to 5° and filtered. The precipitate is washed with water (2×5 ml) and hexane (2×ml). The solids are dried overnight at 60° under reduced pressure to give the title compound, m.p. 217–221 (dec); NMR (CDCl$_3$) 0.95, 1.5, 4.4, 4.5 and 5.7 δ.

EXAMPLE 28

17β-Cyano-9β,11β-epoxy-17α-hydroxyandrost-4-en-3-one 17-(chloromethyl)dimethylsilyl ether (II)

Following the general procedure of EXAMPLES 1 and 3 and making non-critical variations but starting with 17β-cyano-9β,11β-epoxy-17α-hydroxyandrost-4-en-3-one (I), the title compound is obtained.

EXAMPLE 29

17β-Cyano-3,11β,17α-trihydroxyandrosta-3,5-diene 3-ethyl ether 17-(chloromethyl)dimethylsilyl ether (II)

17β-Cyano-3,11β,17α-trihydroxyandrosta-3,5-diene 3-ethyl ether (I, PREPARATION 2) is cooled in a wet ice/acetone bath. Methylene chloride (3 ml) is added followed by a solution of 4-dimethylaminopyridine (0.03 eq) in methylene chloride (0.5 ml). This is followed by the dropwise addition of chloromethyldimethylchlorosilane (1.3 eq). The mixture is stirred at 0°. The reaction mixture is then transferred by cannula into a solution of 1.0M dipotassium phosphate in methylene chloride (50 ml/50 ml) cooled in an ice water bath. The two phases are permitted to separate. The aqueous layer is washed three times with methylene chloride. All the organic phases are combined and backwashed with water, dried over sodium sulfate, concentrated and filtered. The filtrate is column chromatographed on silica gel eluting with ethyl acetate/hexane (10/90). The appropriate fractions are pooled and concentrated to give the title compound.

EXAMPLE 30

17β-Cyano-9β,11β-epoxy-17α-hydroxyandrosta-1,4-dien-3-one 17-(chloromethyl)dimethylsilyl ether (II)

Glacial acetic acid (0.071 ml) is added to a mixture of 9β,11β-epoxyandrosta-1,4-diene-3,17-dione (0, 340.5 mg), potassium cyanide (137.6 mg) in methanol (0.43 ml), water (0.43 ml), and THF (0.14 ml). After 3 hrs at 20°–25°, glacial acetic acid (200 μl), methylene chloride (10 ml) and water (5 ml) are added. The layers are separated and the organic phase is concentrated under reduced pressure. Methylene chloride (1 ml) is added, then distilled off under reduced pressure. DMAP (8.8 mg), methylene chloride (2 ml) and TEA (0.207 ml) are added and the mixture stirred at 20°–25° for 2 hours. The mixture is cooled to $<-5°$ C., and chloromethyldimethylchlorosilane (0.180 ml) is added. After 30 min, aqueous potassium phosphate monobasic (5 ml) is added and the phases separated. The aqueous layer is washed with methylene chloride (5 ml). The organic layers are combined, washed with water (10 ml) and then concentrated under reduced pressure to an oil. The oil is purified by column chromatography eluting with ethyl acetate/hexane (30/70) to give the title compound, m.p. 182°–185°; NMR ($CD_2Cl_2$) 0.4, 1.1, 1.4, 2.9, 3.3, 6.1 and 6.6 δ.

EXAMPLE 31

17β-Cyano-11β,17α-dihydroxyandrosta-1,4-dien-3-one 17-(chloromethyl)dimethylsilyl ether (II)

Following the general procedure of EXAMPLES 1 and 3 and making non-critical variations but starting with 17β-cyano-11β,17α-dihydroxyandrosta-1,4-dien-3-one (I), the title compound is obtained, NMR ($CDCl_3/CD_3OD$) 0.3, 1.2, 1.4, 2.8, 4.4, 6.0, 6.1, 6.3 and 7.3 δ.

EXAMPLE 32

17β-Cyano-17α-hydroxyandrosta-1,4-diene-3,11-dione 17-(chloromethyl)dimethylsilyl ether (II)

Following the general procedure of EXAMPLES 1 and 3 and making non-critical variations but starting with 17β-cyano-17α-hydroxyandrosta-1,4-diene-3,11-dione (I), the title compound is obtained.

EXAMPLE 33

17β-Cyano-17α-hydroxy-6α-methylandrosta-4,9(11)-dien-3-one 17-(chloromethyl)dimethylsilyl ether (II)

Following the general procedure of EXAMPLE 30 and making non-critical variations but starting with 17β-cyano-17α-hydroxy-6α-methylandrosta-4,9(11)-dien-3-one (I), the title compound is obtained, NMR ($CDCl_3$) 0.3, 0.9, 1.1, 1.3, 2.8, 5.5 and 5.8 δ.

EXAMPLE 34

17β-Cyano-9β,11β-epoxy-17α-hydroxy-6α-methylandrost-4-en-3-one 17-(chloromethyl)dimethylsilyl ether (II)

Following the general procedure of EXAMPLES 1 and 3 and making non-critical variations but starting with 17β-cyano-9β,11β-epoxy-17α-hydroxy-6α-methylandrost-4-en-3-one (I), the title compound is obtained.

EXAMPLE 35

17β-Cyano-11β,17α-dihydroxy-6α-methylandrost-4-en-3-one 17-(chloromethyl)dimethylsilyl ether (II)

Following the general procedure of EXAMPLES 1 and 3 and making non-critical variations but starting with 17β-cyano-11β,17α-dihydroxy-6α-methylandrost-4-en-3-one (I, PREPARATION 3), the title compound is obtained, m.p. 238.3°–239.1°; NMR ($CD_2Cl_2/CD_3OD$) 0.3, 1.0, 1.1, 1.4, 2.8, 4.4 and 5.7 δ.

EXAMPLE 36

17β-Cyano-17α-hydroxy-6α-methylandrosta-1,4,9(11)-trien-3-one 17-(chloromethyl)dimethylsilyl ether (II)

Following the general procedure of EXAMPLE 30 and making non-critical variations but starting with 17β-cyano-17α-hydroxy-6α-methylandrosta-1,4,9(11)-trien-3-one (I), the title compound is obtained, m.p. 143°–154°; NMR ($CDCl_3$) 0.3, 0.9, 1.1, 1.4, 2.8, 5.6, 6.1, 6.3 and 7.2 δ.

EXAMPLE 37

17β-Cyano-9β,11β-epoxy-17α-hydroxy-6α-methylandrosta-1,4-dien-3-one 17-(chloromethyl)dimethylsilyl ether (II)

Following the general procedure of EXAMPLE 30 and making non-critical variations but starting with 17β-cyano-9β,11β-epoxy-17α-hydroxy-6α-methylandrosta-1,4-dien-3-one (I), the title compound is obtained, m.p. 161–163; NMR ($CDCl_3$) 0.3, 1.1, 1.2, 1.4, 2.8, 3.3, 6.1, 6.2 and 6.6 δ.

EXAMPLE 38

17β-Cyano-11β,17α-dihydroxy-6α-methylandrosta-1,4-dien-3-one 17-(chloromethyl)dimethylsilyl ether (II)

Chloromethyldimethylchlorosilane (0.092 ml) is added over a period of 1 minute to 17β-cyano-11β,17α-dihydroxy-6α-methylandrosta-1,4-dien-3-one (I, PREPARATION 4, 192.8 mg) and DMAP (8.8 mg) in methylene chloride (0.87 ml) and TEA (0.11 ml) and the mixture cooled to $-12°$. The mixture is stirred for 52 min at $<-8°$, then aqueous potassium phosphate monobasic (3 ml) is added, followed by methylene chloride (5 ml). The layers are separated and the aqueous layer is washed twice with methylene chloride (2 ml). The organic extracts are combined and backwashed with water (5 ml), then concentrated under reduced pressure to give a solid. This solid is dissolved in a minimal amount of hot ethyl acetate then cooled to $<0°$. The resultant crystals are filtered, washed with hexane, and then dried in vacuo at 45° overnight to give the title compound, m.p. 250.5°–251.4°; NMR ($CD_2Cl_2/CD_3OD$) 0.3, 1.1, 1.2, 1.5, 2.9, 4.5, 6.0, 6.3, and 7.45 δ.

EXAMPLE 39

17β-Cyano-6α-fluoro-17α-hydroxyandrosta-4,9(11)-dien-3-one 17-(chloromethyl)dimethylsilyl ether (II)

To 17β-cyano-6α-fluoro-17α-hydroxyandrosta-4,9(11)-dien-3-one (I, PREPARATION 6, 73.8 mg) is added methylene chloride (2.0 ml) and DMAP (4.6 mg). The mixture cooled to $-10°$. TEA (0.049 ml) followed by chloromethyldimethylchlorosilane (0.033 ml) is added. After 5 min, TEA (0.060 ml) is added. After 40 min, aqueous potassium phosphate monobasic (5 ml) followed by methylene chloride (5 ml) is added and the phases separated. The aqueous layer is washed with methylene chloride (5 ml) and the combined organic layers washed with water (10 ml). The organic layer is dried over anhydrous sodium sulphate and filtered through silica gel (1 g). Concentrated hydrochloric acid (15 ml) is then added and the mixture vigorously shaken for 5 min. The layers are separated and the organic layer washed with several portions of water to pH≈6.0. The organic layer is dried over anhydrous sodium sulphate and concentrated to an oil under reduced pressure. Ethyl acetate (1 ml) followed by hexane (1 ml) is added and the mixture cooled to $-10°$ for 5 hrs. The resultant crystals are collected by filtration, washed with hexane, and dried in vacuo at $20°-25°$ to give the title compound, m.p. $131°-132°$ C.; NMR (CDCl$_3$) 0.4, 0.9, 1.4, 2.9, 5.8, and 6.2 δ.

EXAMPLE 40A

17α-Cyano-17β-hydroxy-16-methyleneandrost-4-en-3-one 17-(chloromethyl)dimethylsilyl ether (II)

A slurry of 17α-cyano-17β-hydroxy-16-methyleneandrost-4-en-3-one (I, PREPARATION 7, 2.50 g) and DMAP (0.038 g) in methylene chloride (12.5 ml) is cooled to $-10°$ to $-15°$ while stirring under a nitrogen atmosphere. TEA (1.40 ml) and chloromethyldimethylchlorosilane (1.20 ml) are added to the steroid mixture and the resulting mixture is stirred for 1 hr and then poured in to a mixture of potassium dihydrogen phosphate (1.0M, 15 ml) and methylene chloride (20 ml). The mixture is stirred vigorously at $-10°$ to $-5°$ for 10 min. The layers are then separated and the aqueous layer is extracted with methylene chloride. The organic extracts are washed with water, dried over sodium sulfate and concentrated to the crude product. The product is purified by chromatography on silica gel (230-400 mesh, 400 g) eluting with ethyl acetate/cyclohexane (20/80). The appropriate fractions are pooled and concentrated to give the title compound, NMR (CD$_2$Cl$_2$) 0.42, 0.43, 0.79, 1.19, 2.93, 5.24, 5.40 and 5.67 δ.

EXAMPLE 40B

21-Chloro-17β-hydroxy-16-methylenepregn-4-ene-3,20-dione (III)

Trimethylsilyl chloride (0.32 ml) and LDA (4.99M, 4.4 ml) in a mixture of iso-octanes are added to a solution of 17α-cyano-17β-hydroxy-16-methyleneandrost-4-en-3-one 17-(chloromethyl)dimethylsilyl ether (II, EXAMPLE 40A, 1.0 g) in THF (10 ml). The mixture is stirred for 5 min at $-71°$ then warmed to $-20°$, then cooled to $-71°$ and stirred for 15 min more. The reaction mixture is added to a solution of concentrated hydrochloric acid (4.8 ml) and methanol (8.0 ml) stirring rapidly under a nitrogen atmosphere at $-71°$. After 15 min the resulting mixture is warmed to $20°-25°$ and partitioned between methylene chloride and water. The organic phase is washed with water and dried over sodium sulfate and concentrated. The concentrate is purified by chromatography on silica gel (230-400 mesh, 150 g) eluting with ethyl acetate/cyclohexane (25/75). The appropriate fractions are pooled and concentrated to give the title compound, NMR (CD$_2$Cl$_2$) 0.88, 1.17, 3.0, 4.60, 5.16 and 5.69 δ.

EXAMPLE 40C

17β-Hydroxy-16-methylenepregn-4-ene-3,20-dione (V)

Zinc dust (0.030 mg) and glacial acetic acid (0.13 ml) is added to a solution of 21-chloro-17β-hydroxy-16-methylenepregn-4-ene-3,20-dione (III, EXAMPLE 40B, 0.050 g) in ethyl acetate (1.5 ml). The reaction system is purged with nitrogen and warmed to $45°$. After stirring for 16.5 hr, THF (5 ml) is added and the mixture is filtered thru celite to remove the remaining zinc. The filtrate is then partitioned between water (5 ml) and ether (5 ml). The organic extract is washed with sodium bicarbonate (5%) and water, dried over sodium sulfate and concentrated to give the title compound, NMR (CD$_2$Cl$_2$) 0.87, 1.17, 2.20, 3.40, 5.10 and 5.65 δ.

EXAMPLE 41

17β-Cyano-11β,17α-dihydroxyandrost-4-en-3-one 11-trimethylsilyloxy ether 17-(chloromethyl)dimethylsilyl ether (II)

17β-Cyano-11β,17α-dihydroxyandrosta-4-en-3-one (I, 2.68 gm) is suspended in methylene chloride (10 ml) and imidazole (1.66 gm) is added. After cooling to $0°$, chloro(chloromethyl)dimethylsilane (1.29 ml) is added. After 30 min at $0°$, methanol (0.07 ml) is addedd, and the mixture is warmed to $20°-25°$. Chlorotrimethylsilane (1.55 ml) is added, and after 5 hrs water (2 ml) is added. The organic phase is washed with water (2 ml), dried over anhydrous potassium carbonate, and the solvent is evaporated under vacuum to give the title compound, NMR (CDCl$_3$) 0.1, 0.3, 1.1, 1.3, 2.8, 4.4 and 5.6 δ.

EXAMPLE 42

17β-Cyano-17α-hydroxy-6-methylenandrosta-4,9(11)-dien-3-one 17-(chloromethyl)dimethylsilyl ether (II)

Following the general procedure of EXAMPLE 30 and making non-critical variations but using 6-methylenandrosta-4,9(11)-diene 3,17-dione (0, 18792-JPP-1-A) the title compound is obtained, m.p. $123°-136°$; NMR (CDCl$_3$) 0.4, 0.9, 1.3, 2.8, 5.0, 5.1, 5.6, and 5.9 δ.

EXAMPLE 43

17β-Cyano-17α-hydroxy-6-methylandrosta-4,6,9(11)-trien-3-one 17-(chloromethyl)dimethylsilyl ether (II)

Following the general procedures of EXAMPLE 30 and making non-critical variations but starting with 6-methylandrosta-4,6,9(11)-triene-3,17-dione (O), the title compound is obtained, m.p. $149°-159°$; NMR (CDCl$_3$) 0.3, 0.9, 1.2, 1.8, 2.8, 5.5, 5.8, and 5.9 δ.

EXAMPLE 44

17β-Cyano-11β,17α-dihydroxy-6-methylenandrost-4-en-3-one 17-(chloromethyl)dimethylsilyl ether (II)

Following the general procedure of EXAMPLE 38 and making non-critical variations but using 17β-cyano-11β,17α-dihydroxy-6-methylenandrost-4-en-3-one (I, PREPARATION 8) the title compound is obtained, m.p. $204°-206°$; NMR (CDCl$_3$) 0.3, 1.2, 1.3, 2.8, 4.5, 5.0, and 5.8 δ.

EXAMPLE 45

17β-Cyano-6-fluoro-3,17α-dihydroxyandrosta-3,5,9(11)-triene 3-methyl ether 17-(chloromethyl)dimethylsilyl ether (II)

TEA (0.080 ml) is added to 17β-cyano-6-fluoro-3,17α-dihydroxyandrosta-3,5,9(11)-triene 3-methyl ether (I, PREPARATION 5, 78.5 mg) and DMAP (2.9 mg) in methylene chloride (0.50 ml), and the mixture is cooled to −12°. Chloromethyldimethylchlorosilane (0.033 ml) is added and the mixture stirred at < −10° for 25 min. Chloromethyldimethylchlorosilane (0.033 ml) then TEA (0.035 ml) is added. After 18 min, aqueous potassium phosphate monobasic (4 ml) is added followed by methylene chloride (5 ml). The layers are separated and the aqueous layer washed with methylene chloride (2 ml). The combined organic layers are dried over anhydrous sodium sulphate and filtered. The filtrate is concentrated under reduced pressure to an oil. Column chromatography eluting with ethyl acetate/hexane (5/95) gives the title compound; NMR (CDCl$_3$) 0.4, 0.9, 1.2, 2.9, 3.6, 5.5, and 5.6 δ.

EXAMPLE 46

17β-Cyano-11β,17α-dihydroxyandrosta-1,4-dien-3-one 11-trimethylsilyloxy ether 17-(chloromethyl)dimethylsilyl ether (II)

Following the general procedure of EXAMPLE 41 and making non-critical variations but starting with 17β-cyano-11β,17α-dihydroxyandrosta-1,4-dien-3-one (I), the title compound is obtained.

EXAMPLE 47

17β-Cyano-17α-hydroxyandrosta-1,4,9(11)-trien-3-one 17-(dichloromethyl)dimethylsilyl ether (II)

Following the general procedure of EXAMPLE 70 and making non-critical variations but starting with 17β-cyano-17α-hydroxyandrosta-1,4,9(11)-trien-3-one (I), the title compound is obtained, m.p. 199°–201.5°; NMR (CDCl$_3$) 0.4, 0.5, 1.0, 1.4, 5.3, 5.6, 6.0, 6.2, 6.3 and 7.2 δ.

EXAMPLE 48

17β-Cyano-17α-hydroxyandrost-4-en-3-one 17-(chloromethyl)methoxymethylsilyl ether [mixture of diastereomers at the silicon center] (II)

DMAP (11.3 mg), methylene chloride (1.4 ml) and TEA (0.152 ml) are added to 17β-cyano-17α-hydroxyandrosta-4-en-3-one (I, 284.6 mg) and the mixture cooled to < −5°. Chloromethylmethyldichlorosilane (0.128 ml) is added and the mixture allowed to warm to 20°–25° for 15 min then cooled −10°. TEA (0.16 ml) followed by methanol (0.044 ml) is added and the mixture allowed to warm to 20°–25°. After 50 min, methanol (0.10 ml), methylene chloride (10 ml) and aqueous potassium phosphate monobasic (5 ml) is added and the layers separated. The organic layer is washed with water (5 ml), then concentrated under reduced pressure. The resultant oil is dissolved in 2 ml ethyl acetate, dried over sodium sulphate, filtered and concentrated to an oil under reduced pressure. Crystallization at −10° from a mixture of ethyl acetate and hexane gives crystals which were filtered, then dried under high vacuum to give the title compound, NMR (CDCl$_3$) 0.4, 0.9, 1.2, 2.8, 3.6, and 5.7 δ.

EXAMPLE 49

17β-Cyano-3,17α-dihydroxyandrosta-3,5,9(11)-triene 3-methyl ether 17-(chloromethyl)methoxymethylsilyl ether [mixture of diastereomers at the silicon center] (II)

Following the general procedures of EXAMPLE 48 and making non-critical variations but starting with 17β-cyano-3,17α-dihydroxyandrosta-3,5,9(11)-triene 3-methyl ether (I), the title compound is obtained; NMR (CDCl$_3$) 0.4, 0.9, 1.1, 2.8, 3.6, 5.1, 5.2, and 5.5 δ.

EXAMPLE 50

17β-Cyano-3,17α-dihydroxyandrosta-3,5,9(11)triene 3-methyl ether 17-(chloromethyl)isopropoxymethylsilyl ether [mixture of diastereomers at the silicon center] (II)

DMAP (0.3716 g), methylene chloride (25 ml) and TEA (2.70 ml) are added to 17β-cyano-3,17α-dihydroxyandrosta-3,5,9(11)-triene 3-methyl ether (I) and the mixture cooled to < −5°. Chloromethylmethyldichlorosilane (2.20 ml) is added and the mixture allowed to warm to 20°–25°. After 25 min, the mixture is cooled to −5° and TEA (2.70 ml) then 2-propanol (3.60 ml) is added. After 15 min, aqueous potassium phosphate monobasic (10 ml) is added and the layers separated. The aqueous layer is washed with methylene chloride (5 ml). The combined organic layers are washed with water (5 ml), dried over sodium sulphate, filtered and concentrated to an oil. Column chromatography eluting with ethyl acetate/hexane (2/98) gives the title compound; NMR (CDCl$_3$) 0.4, 0.9, 1.1, 1.2, 2.8, 3.6, 4.2, 5.1, 5.2, and 5.5 δ.

EXAMPLE 51

17β-Cyano-17α-hydroxyandrost-4-en-3-one 17-(chloromethyl)diisopropoxysilyl ether (II)

DMAP (12.3 mg) and methylene chloride (1.0 ml) is added to 17β-cyano-17α-hydroxyandrost-4-en-3-one (I, 266.2 mg) and the mixture is cooled to < −5°. TEA (0.150 ml) followed by chloromethyltrichlorosilane (0.114 ml) is added and the mixture stirred for 25 min. TEA (0.290 ml) is added followed by 2-propanol (0.149 ml). After 5 min, the mixture is warmed to 20°–25°. After 45 min, the reaction mixture is poured into pentane (30 ml) and aqueous potassium phosphate monobasic (7 ml). The reaction flask is rinsed with pentane (10 ml). The layers are separated and the aqueous layer washed with pentane (5 ml). The organic layers are combined, dried over anhydrous sodium sulphate, filtered, and concentrated under reduced pressure. Column chromatography of the concentrate and eluting with ethyl acetate/hexane (10/90) gives the title compound; NMR (CDCl$_3$) 1.0, 1.2, 1.3, 2.8, 4.3, and 5.7 δ.

EXAMPLE 52

17β-Cyano-17α-hydroxyandrosta-4,9(11)-dien-3-one 17-(chloromethyl)diisopropoxysilyl ether (II)

Pentane (3 ml), water (1 ml) and glacial acetic acid (35 ml) is added to 17β-cyano-3,17α-dihydroxyandrosta-3,5,9(11)-triene 3-methyl ether 17-(chloromethyl)diisopropoxysilyl ether (II, EXAMPLE 53, 244 mg). After stirring vigorously for 2 min, the reaction mixture is poured into ethyl acetate (30 ml) and aqueous potassium phosphate monobasic (10 ml). The layers are separated and the organic layer dried over anhydrous sodium sulphate, filtered and concentrated under reduced pressure to give the title compound; NMR (CDCl$_3$) 0.9, 1.2, 1.3, 2.7, 4.3, 5.5, and 5.7 δ.

EXAMPLE 53

17β-Cyano-3,17α-dihydroxyandrosta-3,5,9(11)-triene 3-methyl ether 17-(chloromethyl)diisopropoxysilyl ether (II)

4-Dimethylaminopyridine (0.7013 g) and methylene chloride (50 ml) followed by TEA (32.0 ml) are added to 17β-cyano-3,17α-dihydroxyandrosta-3,5,9(11)-triene 3-methyl ether (I, 18.58 g). When the mixture becomes homogeneous, the mixture is cooled to −10° and chloromethyltrichlorosilane (7.9 ml) is added. The mixture is stirred for 3 hr maintaining the temperature below −5°. The mixture is cooled to −78° and isopropanol (23 ml) is added at such a rate as to maintain the temperature below −10°. The mixture is then stirred at 20°–25° for 2 hr, then poured into pentane (400 ml) over aqueous potassium phosphate monobasic (150 ml). The phases are separated and the aqueous phase is washed with pentane (200 ml). The combined organic phases are washed with water (100 ml) and concentrated to approximately 400 ml under reduced pressure, then cooled to −20° for 3 days. The resultant crystals are removed by vacuum filtration and washed with pentane (100 ml). The mother liquour is dried over anhydrous sodium sulphate, filtered, and concentrated to a oil. This is placed on a silica gel (50 g) column and eluted with ethyl acetate/hexane (2/98, 100 ml). The first 240 ml are discarded and the remaining eluent is concentrated to a clear oil, under reduced pressure. This oil is placed under high vacuum at 20°–25° for 2 days, then allowed to crystallize at −20° for 5 days. The crystals are washed with pentane (2×20 ml) at −20° and dried at 20°–25° under high vacuum for 1 day to give the title compound, m.p. 79°–81°; NMR (CDCl$_3$) 0.9, 1.1, 1.2, 2.7, 3.6, 4.3, 5.1, 5.3, and 5.5 δ.

EXAMPLE 54

17α-Cyano-17β-hydroxyandrosta-4,9(11)-dien-3-one 17-(chloromethyl)dimethylsilyl ether (II)

Following the general procedure of EXAMPLE 40A and making non-critical variations but starting with 17α-cyano-17β-hydroxyandrosta-4,9(11)-dien-3-one (I, PREPARATION 9), the title compound is obtained, m.p. 135.8°–138.8°; NMR (CDCl$_3$) 0.4, 0.8, 1.4, 2.9, 5.6 and 5.7 δ.

EXAMPLE 55

21-Chloro-17β-hydroxypregna-4,9(11)-diene-3,20-dione (III)

Following the general procedure of EXAMPLE 40B and making non-critical variations but starting with 17α-cyano-17β-hydroxyandrosta-4,9(11)-dien-3-one 17-(chloromethyl)dimethylsilyl ether (II, EXAMPLE 54), the title compound is obtained, m.p. 227°–228.5°; NMR (CDCl$_3$) 0.2, 0.7, 2.7, 5.5 and 5.6 δ.

EXAMPLE 56

17β,21-Dihydroxypregna-4,9(11)-diene-3,20-dione 21-acetate (VII)

Following the general procedure of EXAMPLE 18 and making non-critical variations but starting with 21-chloro-17β-hydroxypregna-4,9(11)-diene-3,20-dione (III, EXAMPLE 55) the title compound is obtained, m.p. 175°–176.8°.

EXAMPLE 57

17β-Cyano-17α-hydroxyandrost-5-en-3-one 3-ethylene ketal 17-(bromomethyl)dimethylsilyl ether (II)

Following the general procedure of EXAMPLE 2 and making non-critical variations but starting with 17β-cyano-17α-hydroxyandrost-5-en-3-one 3-ethylene ketal (I, U.S. Pat. No. 4,500,461 Example 3), the title compound is obtained, NMR (CDCl$_3$) 0.4, 0.9, 1.0, 1.5, 2.6, 3.9 and 5.5 δ.

EXAMPLE 58

17β-Cyano-17α-hydroxyandrost-5-en-3-one 3-ethylene ketal 17-(iodomethyl)dimethylsilyl ether (II)

17β-Cyano-17α-hydroxyandrost-5-en-3-one 3-ethylene ketal 17-(bromomethyl)dimethylsilyl ether (II, EXAMPLE 57, 0.857 gm) and sodium iodide (0.52 gm) are taken up in acetone (0.5 ml) and heated at reflux for 3 hrs. The solvent is removed under vacuum and the residue partitioned between ethyl acetate and hexane. The organic phase is separated, dried over anhydrous sodium sulfate, and the solvent removed under vacuum while being replaced with hexane. The product separates to give the title compound, NMR (CDCl$_3$) 0.4, 0.9, 1.0, 2.1, 3.9, and 5.3 δ.

EXAMPLE 59

17β-Cyano-17α-hydroxyandrosta-4,9(11)-dien-3-one 17-(dichloromethyl)dimethylsilyl ether (II)

Following the general procedure of EXAMPLE 1 and making non-critical variations but starting with dichloromethyldimethylchlorosilane, the title compound is obtained, m.p. 165°–174°.

EXAMPLE 60

21,21-Dichloro-17α-hydroxypregna-4,9(11)-diene-3,20-dione (III)

A solution of lithium hexamethyldisilazide (LiHMDS) in THF (1.0 molar, 0.7 ml) is added dropwise to a solution of 17β-cyano-17α-hydroxyandrosta-4,9(11)-dien-3-one 17-(dichloromethyl)dimethylsilyl ether (II, EXAMPLE 59, 0.1095 gm) in THF (1.0 ml) at −65° under nitrogen maintaining the temperature at about −65° to 45°. The temperature is then allowed to warm to 0°. The reaction is cooled again to −45°. The reaction is quenched with a solution of methanol (3 ml) and concentrated hydrochloric acid (3 ml). The reaction is allowed to warm to 20°–25°. The mixture is extracted with methylene chloride. The combined layers are dried over sodium sulfate, filtered and concentrated. The concentrate is chromatographed on silica gel using ethyl acetate hexane (20/80) followed by ethyl acetate/hexane (50/50) to obtain the title compound, NMR (CDCl$_3$) 0.7, 1.3, 5.5, 5.7 and 6.5 δ.

EXAMPLE 61

17α-Hydroxypregna-4,9(11)-diene-3,20-dione (VI)

Dry THF (20 ml) is added to lithium wire (64.1 mg) and 4,4'-di-t-butylbiphenyl (3.047 g) under argon. The mixture is cooled to −10°, then sonicated until it has a persistent blue-green color. The mixture is stirred for 3 hr at −5°, then cooled to −70°. 17β-Cyano-3,17α-dihydroxyandrosta-3,5,9(11)-triene 3-methyl ether 17-(chloromethyl)diisopropoxysilyl ether (II, EXAMPLE 53, 928.0 mg) in THF (20 ml) is added dropwise over 5 min. Immediately, 1,2-dichloroethane (10 ml) followed by methanol (5 ml) and sulphuric acid (6M, 10 ml) are added. The mixture is warmed to 20°-25° and stirred for 20 hrs. The phases are separated and the aqueous phase washed with methylene chloride (30 ml). The combined organic phases are washed with water (2×20 ml). Methanol (30 ml) is added to the organic phase which is then dried over sodium sulfate. The mixture is filtered and concentrated to crystals under reduced pressure. The crystals are triturated with hot pentane (100 ml), collected by vacuum filtration and washed with pentane (3×50 ml). The crystals are dried at 50° for 20 hr to give the title compound; NMR (CDCl$_3$/CD$_3$OD) 0.4, 1.2, 2.0, 5.4, and 5.5 δ.

EXAMPLE 62

17α,21-Dihydroxypregna-4,9(11)-diene-3,20-dione (VII)

To lithium wire (77.9 mg) and 4,4'-di-t-butylbiphenyl (3.780 g) under argon is added THF (30 ml). The mixture is cooled to −10°, then sonicated until it has a persistent blue-green color. The mixture is stirred at −18° for 17 hrs, then cooled to −52°, 17β-cyano-3,17α-dihydroxyandrosta-3,5,9(11)-triene 3-methyl ether 17-(chloromethyl)diisopropoxysilyl ether (II, EXAMPLE 53, 912.3 g) in THF (7 ml) is added dropwise over 2 min. Immediately, 1,2-dichloroethane (0.30 ml) followed by aqueous hydrogen peroxide (30%, 8 ml) is added. The temperature is maintained at less than −10° for 1 hr, then methanol (5 ml) and sulfuric acid (6M, 10 ml) is added. The mixture is then stirred at 20°-25° for 1 hr. Methylene chloride (30 ml) is added and the phases separated. The aqueous layer is washed with methylene chloride (2×10 ml). The organic layers are combined and washed with water (2×20 ml), aqueous sodium thiosulphate (1M, 50 ml) and water (2×50 ml). Methanol (25 ml) is added to the organic phase which is then dried over anhydrous sodium sulphate. The mixture is filtered and concentrated to crystals under reduced pressure. Column chromatography on silica gel eluting with acetone/methylene chloride (5/95) gives the title compound, m.p. 243°-249°; NMR (CDCl$_3$/CD$_3$OD) 0.4, 1.2, 5.4, and 5.5 δ.

EXAMPLE 63

21-Bromo-17α-hydroxypregn-4-ene-3,20-dione (III)

17β-Cyano-3,17α-dihydroxyandrosta-3,5-diene 3-methyl ether 17-(bromomethyl)dimethylsilyl ether (II, EXAMPLE 13, 0.5005 gm) and dry THF (0.7 mls) are cooled to −31°. A solution of LDA in a mixture of iso-octanes (2.07M, 1.0 ml) is added dropwise with stirring over 2 min maintaining the temperature at −31°. After 8 min the reaction is cooled to −70° and quenched by adding a solution of concentrated hydrochloric acid (0.9 ml) and ethylene glycol (0.17 ml). The reaction mixture is warmed to 20°-25° and stirred 18 hr. Cyclohexane (0.6 ml) is added followed by water (2.6 ml). The reaction mixture is filtered and washed with water followed by cyclohexane and dried overnight at 60° to give the title compound, (mixed with the 21-chloro steroid), NMR (CD$_3$OD/CDCl$_3$) 0.6, 1.1, 3.2, 4.3, 4.4, and 5.6 δ.

EXAMPLE 64

21-Bromo-17α-hydroxypregn-4-ene-3,20-dione (III)

Following the general procedure of EXAMPLE 63 and making non-critical variations but using hydrobromic acid in place of hydrochloric acid, the title compound is obtained free of the corresponding 21-chloro steroid, 21-chloro-17α-hydroxypregn-4-ene-3,20-dione.

EXAMPLE 65

21-Bromo-17α-hydroxypregn-4-ene-3,20-dione (III)

Following the general procedure of EXAMPLE 63 and making non-critiacl variations but allowing the reaction mixture to stir for 10 min at 20°-25° followed by quenching give the title compound, substantially free of the corresponding 21-chloro steroid, 21-chloro-17α-hydroxypregn-4-ene-3,20-dione.

EXAMPLE 66

21-Chloro-17α-hydroxypregna-4,9(11)-diene-3,20-dione (III)

3-Hydroxyandrosta-3,5,9(11)-trien-17-one 3-methyl ether (0, U.S. Pat. No. 3,516,991 Example 1, 22.5 g), potassium cyanide (9.1 g), methanol (30.3 ml) and THF (18 ml) are combined and heated to 32°. Acetic acid (6.3 ml) is added over 30 min and the mixture stirred at 32° for 1.5 hr followed by acetic acid (6.3 ml) added over 30 min and stirring for 1 hr. Methanol (3.6 ml) is added over 1 hr and then the mixture is stirred for 30 min. Water (30 ml, 15 ml and 7.5 ml) is added over periods of 1.5 hr, 1.5 hr and 30 min with stirring inbetween additions of water of 4 hr and 0.5 hr respectivly. The mixture is cooled to 0°, acetic acid (2.5 ml) is added and the mixture stirred for 30 min at 0°. Methanol (4.7 ml), water (50 ml) and acetic acid (0.3 ml) are added, the mixture filtered and dried to obtain 17β-cyano-3,17α-dihydroxyandrosta-3,5,9(11)-triene 3-methyl ether (I).

17β-Cyano-3,17α-dihydroxyandrosta-3,5,9(11)-triene 3-methyl ether. (I, 20 g), methylene chloride (140 ml), pyridine in methylene chloride (2 ml in 10 ml) are mixed. Sodium chloride (3.5 g) in water (10 ml) is added and the mixture stirred for 5 min. The phases are separated, the aqueous phase is extracted with methylene chloride (2×10 ml) and the organic phases are combined. The mixture is concentrated by distillating off 85 ml and cooled to 0°. Inidazole (2.5 g) in TEA (8.2 ml) is added followed by slow addition of chloromethyldimethylchlorosilane (10.8 ml) and methylene chloride rinse (1×1 ml, 1×5 ml) maintaining the temperature at 0° +2°. The mixture is degassed, water (110 ml) added and stirred vigorously for 10 min. The phases are separated, the aqueous phase is extracted with methylene chloride (2×10 ml) and combined with the original organic phase. The organic phase is concentrated replacing the methylene chloride with heptane (123 ml) until GC assay shows methylene chloride<1% by volume. The mixture is stirred, cooled to 0° and filtered to give 17β-cyano-3,17α-dihydroxyandrosta-3,5,9(11)-triene 3-methyl ether 17-(chloromethyl)dimethylsilyl ether (II).

The silyl ether (II, 24 g) in THF (62.5 ml) is cooled to −40° and LDA (42 ml) is added slowly keeping the temperature at about −35° t about −40°. Concentrated hydrochloric acid (72 ml) and ethylene glycol (8.75 ml) precooled to< −40° are added maintaining the temperature at 0°. The mixture is hydrolyzed for 1 hr at 20° ±2°. Heptane (16 ml) and water (10 ml) are added the the mixture heated to 50° while stirring for 1 hr. The mixture is cooled to −5° and stirred for 30 min while adding water (2×30 ml). The mixture is filtered and the solid dryed at 60° under nitrogen to give the title compound.

Before disposing of the non-used phases, filtrates, washes etc, a check should be made for cyanide and if necessary treatment with sodium hypochlorite and quenching with sodium sulfite along with proper disposal.

EXAMPLE 67

17β-Cyano-3,17α-dihydroxyandrosta-3,5-diene 3-methyl ether 17-(iodomethyl)dimethylsilyl ether (II)

Following the general procedure of EXAMPLE 58 and making non-critical variations but starting with 17β-cyano-3,17α-dihydroxyandrosta-3,5-diene 3-methyl ether 17-(bromomethyl)dimethylsilyl ether (II, EXAMPLE 13), the title compound is obtained, NMR (CDCl$_3$) 0.4, 0.9, 1.0, 2.0, 3.5, 5.1 and 5.2 δ.

EXAMPLE 68

17α-hydroxyprogesterone (VI)

Sodium metal (0.1507 gm) and anhydrous ammonia (approximately 13 ml) are combined in a dried nitrogen purge flask. The mixture is refluxed to insure all the sodium metal dissolved. 17β-Cyano-17α-hydroxyandrost-5-en-3-one 3-ethylene ketal 17-(chloromethyl)-dimethylsilyl ether (II, EXAMPLE 9, 0.4419 gm) is dissolved in THF (2.0 ml) and is added dropwise over 3 min at −78°. The reaction is quenched with isoprene by adding it dropwise until the color of the reaction changes. Ammonium chloride (0.7537 gm) is added and the reaction is allowed to warm to 20°-25°. The ammonia is removed by reduced pressure and the mixture is cooled and concentrated hydrochloric acid/methanol (2/1, 30 ml) is added. The reaction mixture is stirred overnight. Water is added and an extractive workup using methylene chloride is done. The combined organic layer is back-washed, dried with sodium sulfate and concentrated under reduced pressure to to obtain the title compound. The identity of the title compound is confirmed by comparison with an authentic sample using LC.

EXAMPLE 69

17α-hydroxyprogesterone (VI)

17β-Cyano-17α-hydroxyandrost-5-en-3-one 3-ethylene ketal 17-(iodomethyl)dimethylsilyl ether (II, EXAMPLE 58, 0.4935 gm) is mixed with THF (2.0 ml) and cooled to −78°. A solution of butyllithium in hexanes (1.6 molar, 0.89 ml) is added over 2 min. The reaction is stirred until complete as measured by TLC. A solution of methanol (10 ml) and concentrated hydrochloric acid (10 ml) is added to quench the reaction allowing the temperature to reach 5°. The reaction is stirred at 20°-25° until complete by TLC and LC. Heptane is added to the reaction (2.5 to 5 ml). The mixture is concentrated under reduced pressure while adding water. The resulting slurry is cooled, filtered, washed with water and hexane. The solids are dried under reduced pressure to give the title compound. The identity of the title compound is confirmed by comparison with an authentic sample using TLC (silica gel and acetone/-methylene chloride, 10/90) Rf=0.5.

EXAMPLE 70

17β-Cyano-17α-hydroxyandrosta-5,9(11)-dien-3-one 3-ethylene ketal 17-(dichloromethyl)dimethylsilyl ether (II)

TEA (1.00 ml) is added to 17β-cyano-17α-hydroxyandrosta-5,9(11)-dien-3-one 3-ethylene ketal (I, PREPARATION 10, 1.586 g) and 4-dimethylaminopyridine (49.5 mg) in methylene chloride (5.0 ml) and the mixture cooled to −10°. Dichloromethyldimethylchlorosilane (0.875 ml) is then added over 20 seconds. The mixture is stirred for 2 hr below −5° then aqueous monobasic potassium phosphate (15 ml) is added to adjust the pH to 7 followed by ethyl acetate (10 ml). The phases are separated and the aqueous layer is washed with ethyl acetate (10 ml). The combined organic phases are washed with water (10 ml), dried using anhydrous sodium sulphate, filtered and concentrated to a oil. Hexane (5 ml) is added and the mixture allowed to crystallize at 20°-25°. The crystals are collected by vacuum filtration, washed with hexane (2×20 ml) and dried under vacuum at 45° for 18 hr to give the title compound, m.p. 131°-134°; NMR (CDCl$_3$) 0.5, 0.9, 1.3, 4.0, 5.3, 5.4, and 5.5 δ.

EXAMPLE 71

17β-Cyano-17α-hydroxyandrosta-5,9(11)-dien-3-one 3-ethylene ketal 17-(chloromethyl)dimethylsilyl ether (II)

Following the general procedure of EXAMPLES 1 and 3 and making non-critical variations but starting with 17β-cyano-17α-hydroxyandrosta-5,9(11)-dien-3-one 3-ethylene ketal (I), the title compound is obtained.

EXAMPLE 72

17β-Cyano-17α-hydroxyandrosta-5,9(11)-dien-3-one 3-ethylene ketal 17-(bromomethyl)dimethylsilyl ether (II)

Following the general procedure of EXAMPLES 2 and making non-critical variations but starting with 17β-cyano-17α-hydroxyandrosta-5,9(11)-dien-3-one 3-ethylene ketal (I); the title compound is obtained.

EXAMPLE 73

17α-hydroxyprogesterone (VI)

A mixture of 17β-cyano-17α-hydroxyandrost-5-en-3-one 3-ethylene ketal 17-(bromomethyl)dimethylsilyl ether (II, EXAMPLE 57, 360.7 mg) and magnesium powder (180 mg) in dry THF (3 ml) is treated with methyl iodide (0.020 ml) and dibromoethane (0.030 ml). The mixture is sonicated briefly. Dibromoethane (0.25 ml) is added dropwise with stirring and slight heating to maintain a reflux. The resulting slurry is taken up in THF, and the mixture quenched with aqueous hydrochloric acid (6 molar)/methanol (1/1, 5 ml). The solvent is replaced with water by distillation, the mixture filtered to give the title compound, which is identical to an authentic sample by TLC (silica gel, acetone/methylene chloride, 5/95), R$_f$=0.44.

EXAMPLE 74

21-Chloro-17α-hydroxypregna-4,9(11)-diene-3,20-dione (III)

17β-Cyano-17α-hydroxyandrosta-4,9(11)-dien-3-one (I, 3.316 gm) and 4-dimethylaminopyridine (63 mg) are slurried in dry THF (5 ml), treated with TEA (1.9 ml) and immediately cooled in an ice-acetone bath. With rapid stirring chloromethyldimethylchlorosilane (1.54 ml) is added dropwise. After 1 hr, the mixture is allowed to warm to 20°-25° over the course of 2 hrs, giving a mixture containing 17β-cyano-17α-hydroxyandrosta-4,9(11)-dien-3-one 17-(chloromethyl)dimethylsilyl ether (II). This mixture is transferred dropwise (10 min) to a solution of LDA (which is prepared from diisopropyl amine [7.0 ml] and 7-butyllithium-hexanes [1.6 molar, 26.6 ml, 42.6 mmol]) in dry THF (75 ml), stirring rapidly in a dry ice-acetone bath. After stirring 1 hr, the mixture is quenched with aqueous hydrochloric acid (6M, 25 ml), allowing the exotherm to carry the temperature to about 0°. Water (~50 ml) and methanol (~50 ml) are added, and the mixture is allowed to stir vigorously for 20 hrs at 20°–25°. The product is recovered by filtration and washed successively with water and methanol to give the title compound. A second crop is obtained on concentrating the mother liquors.

EXAMPLE 75

21-Chloro-6α-fluoro-17α-hydroxypregna-4,9(11)-diene-3,20-dione (III)

Following the general procedure of EXAMPLE 5 and making non-critical variations but starting with 17β-cyano-6α-fluoro-17α-hydroxyandrosta-4,9(11)-dien-3-one 17-(chloromethyl)dimethylsilyl ether (II, EXAMPLE 39), the title compound is obtained.

EXAMPLE 76

21-Chloro-17α-hydroxy-6α-methylpregna-4,9(11)-diene-3,20-dione (III)

Following the general procedure of EXAMPLE 5 and making non-critical variations but starting with 17β-cyano-17α-hydroxy-6α-methylandrosta-4,9(11)-dien-3-one 17-(chloromethyl)dimethylsilyl ether (II, EXAMPLE 33), the title compound is obtained.

EXAMPLE 77

21-Chloro-17α-hydroxy-6α-methylpregna-1,4,9(11)-triene-3,20-dione (III)

Following the general procedure of EXAMPLE 17 and making non-critical variations but starting with 17β-cyano-17α-hydroxy-6α-methylandrosta-1,4,9(11)-trien-3-one 17-(chloromethyl)dimethylsilyl ether (II, EXAMPLE 36), the title compound is obtained.

EXAMPLE 78

21-Chloro-17α-hydroxypregna-4,9(11)-diene-3,20-dione (III) and 17α-hydroxypregna-4,9(11)-diene-3,20-dione (VI).

THF (15 ml) is added to lithium wire (49.6 mg) and 4,4'-di-tert-butylbiphenyl (2.337 g) under argon. The mixture is cooled to −10°, then sonicated until it has a persistent blue-green color and stirred at −20° for 18 hr, then cooled to −78°. A solution of 17β-cyano-17α-hydroxyandrosta-5,9(11)-dien-3-one 3-ethylene ketal 17-(dichloromethyl)dimethylsilyl ether (II, EXAMPLE 70, 338.1 mg) in THF (10 ml) at −78° is added rapidly. Immediately, 1,2-dichloroethane (1.2 ml) followed by methanol (3.3 ml) in sulfuric acid (6M, 7.7 ml) is added. The mixture is stirred at 20°–25° for 2 days, then methylene chloride (50 ml) and water (50 ml) is added. The phases are separated and the aqueous layer washed with methylene chloride (10 ml). The combined organic layers are washed with water (2×20 ml), then concentrated to an oil under reduced pressure to and chromatographed by reversed phase gradient HPLC to obtain the title compound (III), retention time=13.48 min (consistent with an authentic sample), other appropriate fractions are pooled and concentrated to give the title compound (VI).

EXAMPLE 79

21-Chloro-11β,17α-dihydroxypregn-4-ene-3,20-dione (III)

Following the general procedure of EXAMPLE 5 and making non-critical variations but starting with 17β-cyano-11β,17α-dihydroxyandrost-4-en-3-one 17-(chloromethyl)dimethylsilyl ether (II, EXAMPLE (25) and using 3.8 equivalents of LDA and trimethylsilylchloride, the title compound is obtained, m.p. 247°–249°.

EXAMPLE 80

21-Chloro-11β,17α-dihydroxypregna-1,4-diene-3,20-dione (III)

Following the general procedure of EXAMPLE 17 and making non-critical variations but starting with 17β-cyano-11β,17α-dihydroxyandrosta-1,4-dien-3-one 17-(chloromethyl)dimethylsilyl ether (II, EXAMPLE 31) and using 2 equivalents of LiHMDS and 3.8 equivalents of LDA, the title compound is obtained, m.p. 238°–240°.

EXAMPLE 81

21-Chloro-11β,17α-dihydroxypregn-4-ene-3,20-dione (III)

Following the general procedure of EXAMPLE 5 and making non-critical variations but starting with 17β-cyano-11β,17α-dihydroxyandrost-4-en-3-one 11-dimethylsilyloxy ether 17-(chloromethyl)dimethylsilyl ether (II, EXAMPLE 41) and using 2.8 equivalents of LDA and 1 equivalent of trimethylsilylchloride, the title compound is obtained, m.p. 247°–249°.

EXAMPLE 82

17β-Cyano-9α-fluoro-11β,17α-dihydroxyandrosta-1,4-dien-3-one 17-(chloromethyl)dimethylsilyl ether (II)

Following the general procedure of EXAMPLE 17 and making non-critical variations but starting with 17β-cyano-6α-fluoro-11β,17α-dihydroxyandrosta-1,4-dien-3-one (I), the title compound is obtained, m.p. 267°–274°.

EXAMPLE 83

21-Chloro-11β,17α-dihydroxy-6α-methylpregna-1,4-diene-3,20-dione (III)

Following the general procedure of EXAMPLE 17 and making non-critical variations but starting with 17β-cyano-11β,17α-dihydroxy-6α-methylandrosta-1,4-dien-3-one 17-(chloromethyl)dimethylsilyl ether (II, EXAMPLE 38), the title compound is obtained.

EXAMPLE 84

Pregna-4,9(11)-diene-3,20-dione (V)

Following the general procedure of EXAMPLE 23 and making non-critical variations but starting with 17β-cyano-3-ethoxy-17α-hydroxyandrosta-3,5,9(11)-triene 17-(chloromethyl)dimethylsilyl ether (II, EXAMPLE 10), the title compound is obtained.

EXAMPLE 85

17β-Cyano-9α,17α-dihydroxyandrost-4-en-3-one (I)

Acetone cyanohydrin (1.37 ml) is added to a mixture of 9α-hydroxyandrost-4-ene-3,17-dione (0, U.S. Pat. No. 3,065,146, 3.024 g) in methanol (10 ml). The mixture is stirred at about 35°-39° for about 2 hr, then at about 4°-54° for 1.25 hr. 0.1 ml of a potassium cyanide solution (1 g in 2.0 ml of water) is added and the mixture stirred at about 50°-55° for 30 min and then allowed to stand at 20°-25° overnight. The solids are collected, washed well with methanol and dried under reduced pressure at about 55° for 3 hr to give the title compound, NMR (CDCl$_3$/DMSO-d$_6$; 10/1) 5.8, 2.4, 1.3 and 1.0 δ.

EXAMPLE 86

17β-Cyano-17α-hydroxyandrosta-4,9(11)-dien-3-one (I)

17β-Cyano-9α,17α-dihydroxyandrost-4-en-3-one (I, EXAMPLE 85, 313 mg) is added to sulfuric acid (57%, 5 ml) at 2° and is stirred at 2°-5° for several hr and then overnight at 22°; solids formed. Water (10 ml) is added at 10°, the mixture stirred for 15 min, the solids collected and air dried to give the title compound, NMR (CDCl$_3$/DMSO-d$_6$; 5/1) 5.7, 5.6, 1.4 and 0.9 δ.

EXAMPLE 87

17β-Cyano-9α,17α-dihydroxyandrost-4-en-3-one (I)

Glacial acetic acid (2.87 ml) is added to 9α-hydroxyandrost-4-ene-3,17-dione (0, 13.49 g) and potassium cyanide (4.98 g) slurried in methanol (45 ml) and stirred at 20°-25°. Glacial acetic acid (0.92 ml) is added followed by water (30 ml) over 13.7 hr via a syringe pump, keeping the mixture at 27°. The mixture is stirred an additional 2 hr at 27°. Additional glacial acetic acid (1.5 ml) is added at 15° followed by water (50 ml) at 10°. The mixture is stirred at 10° for 20 min and the product collected by vacuum filtration and washed with water. The solid is dried in an air stream for 24 hr to give the title compound, mp 229°-230°.

EXAMPLE 88

17β-Cyano-17α-hydroxyandrosta-4,9(11)-dien-3-one (I)

A mixture of sulfuric acid (37 ml) and water (32.1 ml) is added to 17β-cyano-9α,17α-dihydroxyandrost-4-en-3-one (I, EXAMPLE 87, 13.28 g). The mixture is stirred at 20°-25° for 19 hr, stirred at 30° for 4 hr, then cooled to 10°. Sulfuric acid (11.2 ml) is added, the mixture is stirred at 20°-25° for 45 min, then cooled to 0° and water (55 ml) is added, maintaining the temperature at <5°. The product is collected by vacuum filtration and washed with water (80 ml), aqueous ammonium acetate (1M, 80 ml) and water (80 ml). The solid is dried in an air stream for 24 hr to give the title compound, mp 225°-228°.

EXAMPLE 89

17β-Cyano-9α,17α-dihydroxyandrost-4-en-3-one (I)

Sulfuric acid (2.07 ml) is added to 9α-hydroxyandrost-4-ene-3,17-dione (I, 21.14 g) and potassium cyanide (6.70 g) slurried in methanol (71.5 ml) and water (6.8 ml) at <5°. The mixture is allowed to warm to 15° over 0.5 hr, then warmed to 30° over 1 hr. The mixture is stirred at 30° for 2.5 hr, then cooled to 2° and sulfuric acid (0.32 ml) is added. The mixture is then stirred at 30° for 2 hr and water (13 ml) is added. Next, water (52 ml) is added over 12 hr, maintaining the mixture at 30°. The mixture is stirred 5 hr at 30°, then cooled to 0° and quenched with sulfuric acid (1 ml). Methanol (89 ml) is added and the mixture is heated to 55°. The solvent is then removed by reduced pressure until the boiling point begins to rise rapidly. The mixture is then cooled to 32° and water (105 ml) is added over 12 min. The mixture is further cooled to 0° and the the solids are collected by vacuum filtration and washed with water to give the title compound, mp 230°-233° (with decomposition).

CHART A

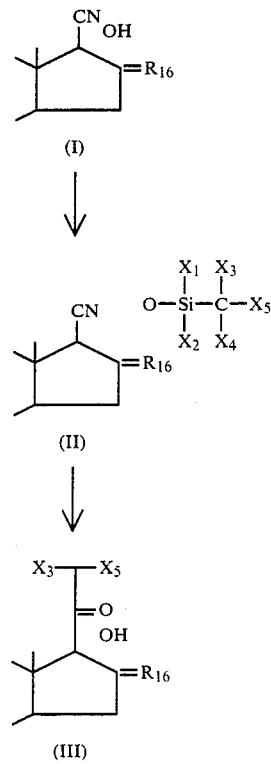

CHART B

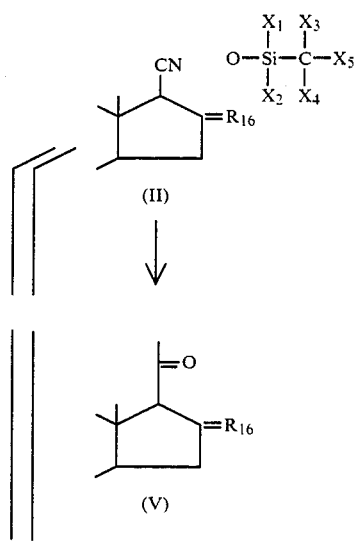

-continued
CHART B
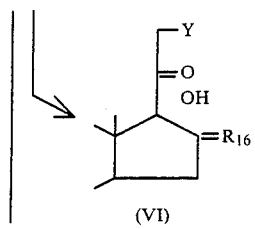
(VI)
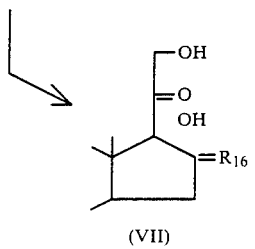
(VII)
CHART C
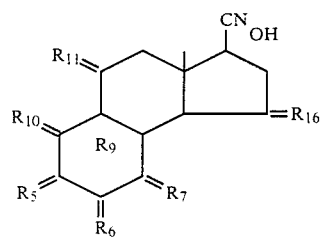
(IA)
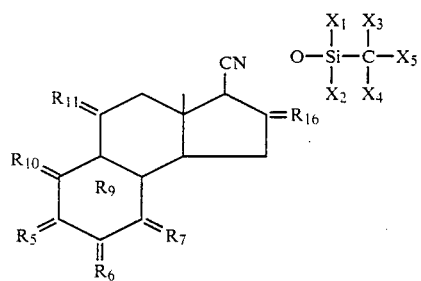
(IIA)
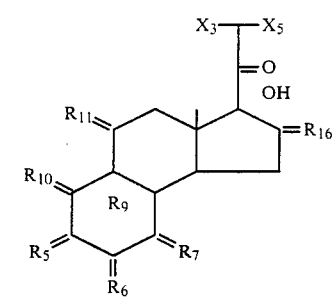
(IIIA)
CHART D
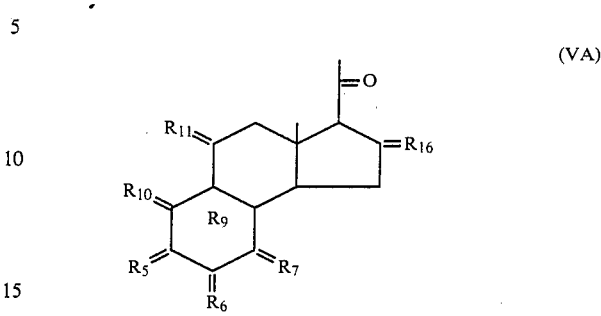
(VA)
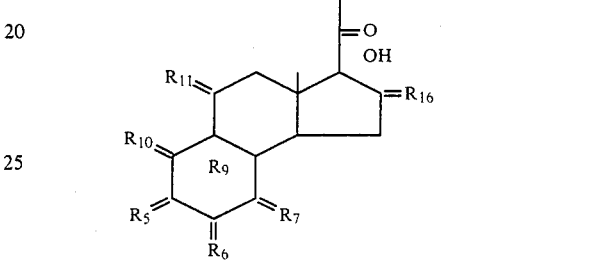
(VIA)
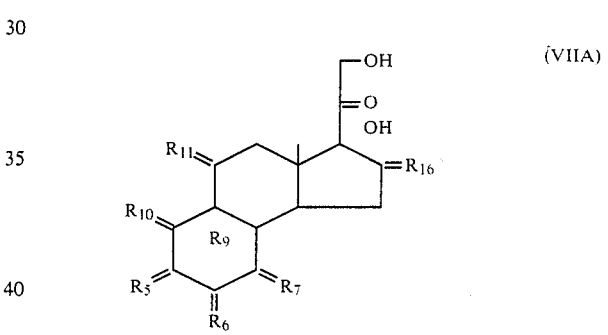
(VIIA)
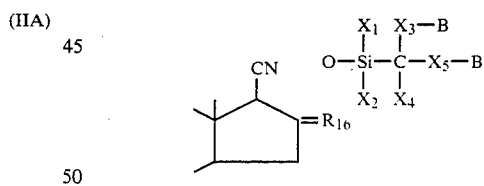
(IIB)
CHART E
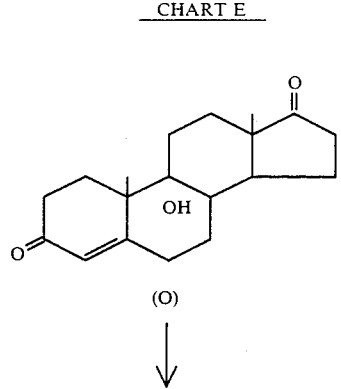
(O)

-continued
CHART E
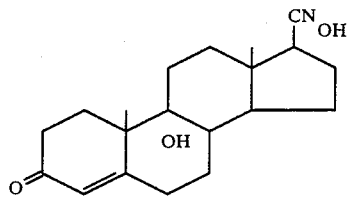
(I)
↓
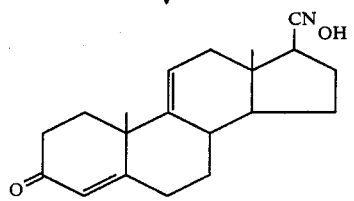
(I)
We claim:
1. 17β-Cyano-9α,17α-dihydroxyandrost-4-en-3-one.
* * * * *